(12) United States Patent
Kimura et al.

(10) Patent No.: US 10,617,301 B2
(45) Date of Patent: Apr. 14, 2020

(54) INFORMATION PROCESSING DEVICE AND INFORMATION PROCESSING METHOD

(71) Applicant: SONY CORPORATION, Tokyo (JP)

(72) Inventors: Natsuki Kimura, Tokyo (JP); Akiko Shimizu, Tokyo (JP); Yuichi Kageyama, Tokyo (JP); Yusuke Nakamura, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 248 days.

(21) Appl. No.: 15/524,765

(22) PCT Filed: Oct. 30, 2015

(86) PCT No.: PCT/JP2015/080666
§ 371 (c)(1),
(2) Date: May 5, 2017

(87) PCT Pub. No.: WO2016/076140
PCT Pub. Date: May 19, 2016

(65) Prior Publication Data
US 2017/0319065 A1     Nov. 9, 2017

(30) Foreign Application Priority Data

Nov. 14, 2014   (JP) ................................ 2014-231798

(51) Int. Cl.
*A61B 5/00*         (2006.01)
*G06K 9/00*         (2006.01)
(Continued)

(52) U.S. Cl.
CPC .............. *A61B 5/004* (2013.01); *A45D 44/00* (2013.01); *A61B 5/0077* (2013.01);
(Continued)

(58) Field of Classification Search
CPC .................. A61B 5/004; A61B 5/6898; A61B 5/441–447; A61B 5/684–6842;
(Continued)

(56) References Cited

U.S. PATENT DOCUMENTS

| 6,571,003 B1 | 5/2003 | Hillebrand et al. |
| 2009/0196475 A1* | 8/2009 | Demirli .................. A61B 5/441 382/128 |

(Continued)

FOREIGN PATENT DOCUMENTS

| AT | 459292 T | 3/2010 |
| AT | 502572 T | 4/2011 |

(Continued)

OTHER PUBLICATIONS

Extended European Search Report of EP Patent Application No. 15858339.3, dated Jun. 13, 2018, 08 pages.

*Primary Examiner* — Catherine B Kuhlman
(74) *Attorney, Agent, or Firm* — Chip Law Group

(57) ABSTRACT

The present technology relates to an information processing device and an information processing method capable of facilitating fixed-point observation on skin condition. The information processing device acquires an image that shows a predetermined feature point of a user who is a measurer of skin condition, and a measurement portion of skin condition, and analyzes the image, and then recognizes a position of the feature point. Furthermore, information indicating the measurement portion is displayed at a predetermined position on the image while setting, as a reference, the recognized position of the feature point. The present technology is applicable to information processing devices such as a tablet terminal, a smartphone, and a personal computer.

14 Claims, 29 Drawing Sheets

(51) Int. Cl.
A45D 44/00 (2006.01)
A61B 5/107 (2006.01)

(52) U.S. Cl.
CPC .......... *A61B 5/1071* (2013.01); *A61B 5/1072* (2013.01); *A61B 5/1079* (2013.01); *A61B 5/441* (2013.01); *A61B 5/684* (2013.01); *A61B 5/748* (2013.01); *A61B 5/7425* (2013.01); *G06K 9/00201* (2013.01); *G06K 9/00234* (2013.01); *A45D 2044/007* (2013.01); *A61B 5/6898* (2013.01); *A61B 2576/02* (2013.01); *G06K 9/00281* (2013.01)

(58) Field of Classification Search
CPC .............. A61B 5/70–78; A61B 5/0077; A45D 2044/007; G06K 9/00221–00315; G06T 7/0016; G06T 2207/30088
See application file for complete search history.

(56) References Cited

U.S. PATENT DOCUMENTS

| | | |
|---|---|---|
| 2009/0201365 A1 | 8/2009 | Fukuoka et al. |
| 2014/0275948 A1* | 9/2014 | Kamisoyama ....... A61B 5/6898 600/407 |
| 2015/0235359 A1 | 8/2015 | Higashitsutsumi et al. |
| 2015/0373264 A1* | 12/2015 | Anzue ................. H04N 5/23293 348/333.05 |
| 2016/0262624 A1* | 9/2016 | Nakajima et al. ..... A61B 5/444 |
| 2017/0076444 A1* | 3/2017 | Petit ........................ A61B 5/441 |
| 2017/0337678 A1 | 11/2017 | Higashitsutsumi et al. |

FOREIGN PATENT DOCUMENTS

| | | |
|---|---|---|
| AU | 5598000 A | 1/2001 |
| BR | 0012216 A | 8/2002 |
| CN | 1355680 A | 6/2002 |
| CN | 1781448 A | 6/2006 |
| CN | 101083940 A | 12/2007 |
| CN | 101711674 A | 5/2010 |
| CN | 104684461 A | 6/2015 |
| EP | 1189536 A1 | 3/2002 |
| EP | 1813189 A1 | 8/2007 |
| ES | 2363759 T3 | 8/2011 |
| HK | 1108345 A1 | 10/2010 |
| HK | 1144367 A1 | 12/2012 |
| JP | 2001-000419 A | 1/2001 |
| JP | 2006-081847 A | 3/2006 |
| JP | 2007-133518 A | 5/2007 |
| JP | 2007-289659 A | 11/2007 |
| JP | 2008-102137 A | 5/2008 |
| JP | 2011-053587 A | 3/2011 |
| JP | 2012-239768 A | 12/2012 |
| JP | 2014-061057 A | 4/2014 |
| JP | 2014-180305 A | 9/2014 |
| KR | 10-2007-0083735 A | 8/2007 |
| KR | 10-2015-0058194 A | 5/2015 |
| MX | PA01012946 A | 7/2002 |
| TW | 201414455 A | 4/2014 |
| WO | 00/76398 A1 | 12/2000 |
| WO | 2006/043702 A1 | 4/2006 |
| WO | 2014/045558 A1 | 3/2014 |

* cited by examiner

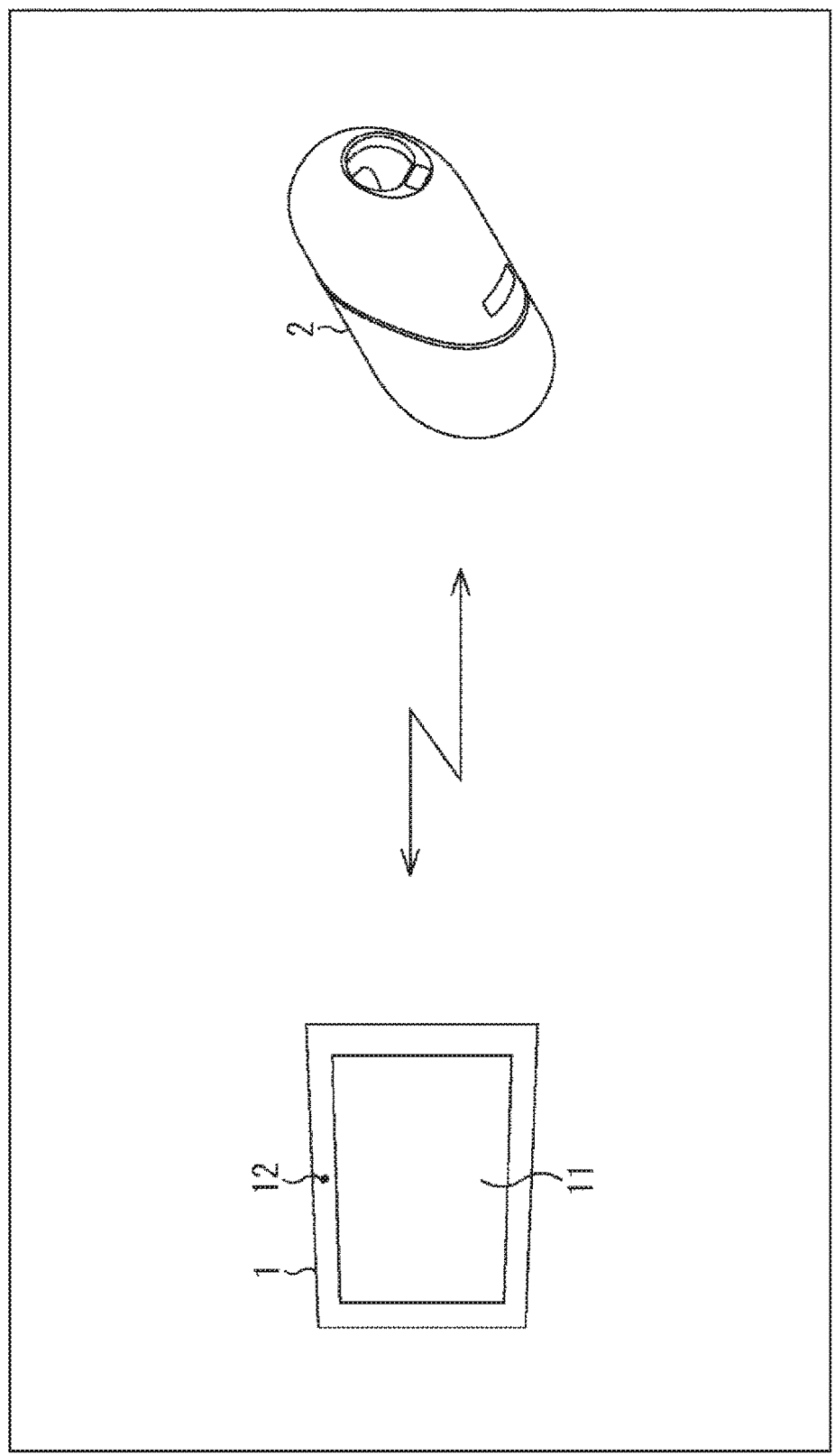

FIG. 10

| SETTING INFORMATION | |
|---|---|
| ·ANGLE | POSITION, DISTANCE |
| ·FEATURE POINT 1 (LEFT EYE) | POSITION, DISTANCE |
| ·FEATURE POINT 2 (RIGHT EYE) | POSITION, DISTANCE |
| ·FEATURE POINT 3 (MOUTH) | POSITION, DISTANCE |
| ·FIXED-POINT OBSERVATION POINT 1 | POSITION, DISTANCE |
| ·FIXED-POINT OBSERVATION POINT 2 | POSITION, DISTANCE |
| ·FIXED-POINT OBSERVATION POINT 3 | POSITION, DISTANCE |

FIG. 25

| | 20140101 23:00:00 | | | 20140108 19:00:00 | | | ... |
|---|---|---|---|---|---|---|---|
| MEASUREMENT DATE/TIME | | | | | | | |
| FILE NAME OF FACE IMAGE | | | | | | | |
| FIXED-POINT OBSERVATION POINT | 1 | 2 | 3 | 1 | 2 | 3 | |
| FILE NAME OF SKIN IMAGE | | | | | | | |
| • COLOR | | | | | | | |
| • TEXTURE | | | | | | | |
| • MOISTURE CONTENT | | | | | | | |
| • OIL CONTENT | | | | | | | |
| • PORE CONDITION | | | | | | | |
| • MELANIN CONTENT | | | | | | | |
| • BLOOD FLOW RATE | | | | | | | |
| • SKIN TEMPERATURE | | | | | | | |

FIG. 28
```
START COMPARISON DISPLAY PROCESSING
        ↓
SELECT FIXED-POINT OBSERVATION POINT              S101
        ↓
SELECT COMPARING CONDITIONS                       S102
        ↓
READ FACE IMAGES OBTAINED WHEN SKIN CONDITION     S103
SATISFYING COMPARING CONDITIONS IS MEASURED
        ↓
DISPLAY FACE IMAGES SIDE BY SIDE                  S104
        ↓
       END
```
FIG. 29
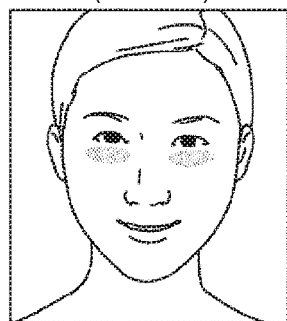
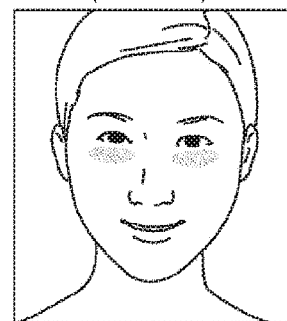
COMPARISON RESULT
PREVIOUS MEASUREMENT (20140101) — 201
CURRENT MEASUREMENT (20140108) — 202

INFORMATION PROCESSING DEVICE AND INFORMATION PROCESSING METHOD

CROSS REFERENCE TO RELATED APPLICATIONS

This application is a U.S. National Phase of International Patent Application No. PCT/JP2015/080666 filed on Oct. 30, 2015, which claims priority benefit of Japanese Patent Application No. JP 2014-231798 filed in the Japan Patent Office on Nov. 14, 2014. Each of the above-referenced applications is hereby incorporated herein by reference in its entirety.

TECHNICAL FIELD

The present technology relates to an information processing device, an information processing method, and a program, and particularly relates to the information processing device, information processing method, and program capable of facilitating fixed-point observation on skin condition.

BACKGROUND ART

There is a technology in which skin condition is measured by analyzing a skin image obtained by photographing skin. A person who performs measurement places a measurement device equipped with an imaging element on a face or the like of a person subjected to measurement, and photographs a measurement portion.

CITATION LIST

Patent Document

Patent Document 1: Japanese Patent Application Laid-Open No. 2012-239768 A

SUMMARY OF THE INVENTION

Problems to be Solved by the Invention

It would be convenient when a user can independently photograph own skin and measure the skin condition. In the case where a user can independently perform measurement, the user can easily observe, for example, change of daily skin condition.

In order to observe change of the skin condition, a same portion is needed to be repeatedly photographed, however; it may be difficult to remember the exact portion.

The present technology is made considering the above-described situation, and directed to achieving facilitation of fixed-point observation on skin condition.

Solutions to Problems

An information processing device according to an aspect of the present technology includes:

an acquisition unit adapted to acquire an image that shows a predetermined feature point of a user who is a measurer of skin condition, and a measurement portion of skin condition;

a recognition unit adapted to analyze the image and recognize a position of the feature point; and a display control unit adapted to display information indicating the measurement portion at a predetermined position on the image while setting, as a reference, the position of the feature point recognized by the recognition unit.

A photographing unit adapted to photograph the image can be further provided. In this case, the acquisition unit can be made to acquire the image photographed by the photographing unit.

A display unit adapted to display the image and the information indicating the measurement portion can be further provided.

It is possible to further provide a setting unit adapted to set the measurement portion at the predetermined position while setting, as a reference, the position of the feature point recognized by the recognition unit by analyzing the image photographed at the time of setting the measurement portion.

It is possible to further provide a setting unit adapted to set the measurement portion at a position designated by the user on the image photographed at the time of setting the measurement portion.

A detection unit adapted to detect an angle of the information processing device at the time of setting the measurement portion can be further provided.

The display control unit can display information to provide a guide on adjusting an angle of the information processing device to an angle same as the angle detected by the detection unit.

The display control unit can display, on the image, information indicating the feature point at a position same as the position of the feature point recognized by the recognition unit by analyzing the image photographed at the time of setting the measurement portion.

The display control unit can change a display position of the information indicating the measurement portion in accordance with change of the position of the feature point.

The acquisition unit can acquire a skin image obtained by photographing skin of the measurement portion, and the display control unit can display the skin image and the image showing the user at the same time.

It is possible to further provide: an analysis unit adapted to analyze the skin image and measure skin condition of the measurement portion; and a recording unit adapted to record information indicating a measurement result obtained by the analysis unit.

The display control unit can display information indicating change of skin condition of the measurement portion on the basis of information indicating results obtained from plural times of measurement recorded in the recording unit.

According to an aspect of the present technology, acquired is an image that shows: a predetermined feature point of a user who is a measurer of skin condition; and a measurement portion of skin condition. Additionally, the image is analyzed, and the position of the feature point is recognized, and then the information indicating the measurement portion is displayed at a position on the image represented while setting the recognized position of the feature point as a reference.

Effects of the Invention

According to the present technology, a user can easily perform fixed-point observation on skin condition.

Note that effects recited herein are not necessarily limited thereto and may be any of those recited in the present disclosure.

BRIEF DESCRIPTION OF DRAWINGS

FIG. 1 is a diagram illustrating an exemplary configuration of a skin condition measurement system to which the present technology is applied.

FIG. 10 is a diagram illustrating exemplary setting information.

FIG. 25 is a diagram illustrating an exemplary measurement result.

FIG. 28 is a flowchart to describe comparison display processing.

FIG. 29 is a diagram illustrating an exemplary face image display screen.

MODE FOR CARRYING OUT THE INVENTION

In the following, a mode to implement the present technology will be described. Note that the description will be provided in the following order.

1. Configuration of Skin Condition Measurement System
2. Configuration of Respective Devices
3. Operation of Information Processing Device
4. Exemplary Classification Using Skin Condition Information
5. Modified Example 1. Configuration of Skin Condition Measurement System FIG. 1 is a diagram illustrating an exemplary configuration of a skin condition measurement system to which the present technology is applied.

The skin condition measurement system in FIG. 1 is formed of an information processing device 1 and a skin measurement device 2. The information processing device 1 and the skin measurement device 2 are connected via wireless communication such as a wireless local area network (LAN). The information processing device 1 and the skin measurement device 2 may also be connected via wired communication using a universal serial bus (USB) cable and the like.

The skin condition measurement system in FIG. 1 is mainly used in order that a user may independently measure own skin condition and confirm a measurement result. The user is a measurer of the skin condition and also a person subject to measurement.

The information processing device 1 is a tablet terminal. The information processing device 1 is provided with a display 11 such as a liquid crystal display (LCD). A camera 12 is provided at a bezel portion of the display 11. Other portable terminals such as a smartphone and a personal computer each equipped with a camera on a surface same as a display surface may also be used as the information processing device 1.

The information processing device 1 acquires a skin image photographed by the skin measurement device 2, and measures skin condition of a user by analyzing the acquired skin image. The skin image is an image that shows the skin in a magnified manner. The information processing device 1 displays, on the display 11, information related to the measured skin condition and presents the information to the user.

The skin measurement device 2 is an electronic device having a size that can be held by a single hand of the user. The skin measurement device 2 is provided with an imaging element and various kinds of sensors such as a body temperature sensor.

Figure 2A:
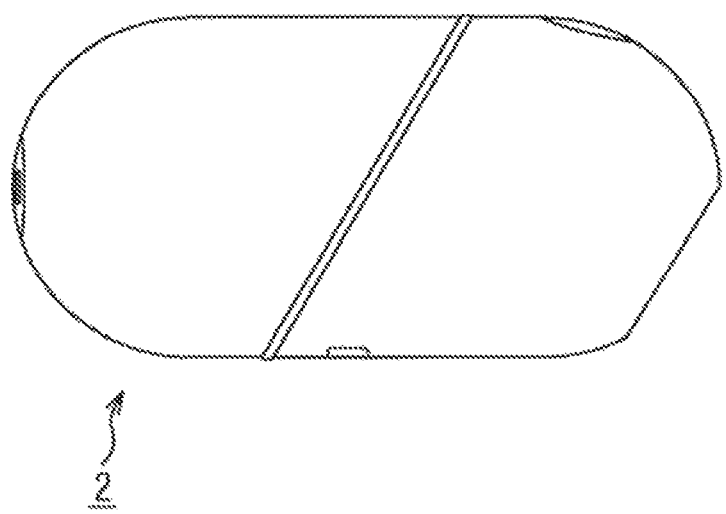
FIGS. 2A and 2B are diagrams illustrating an external view of a skin measurement device.
Figure 2B:
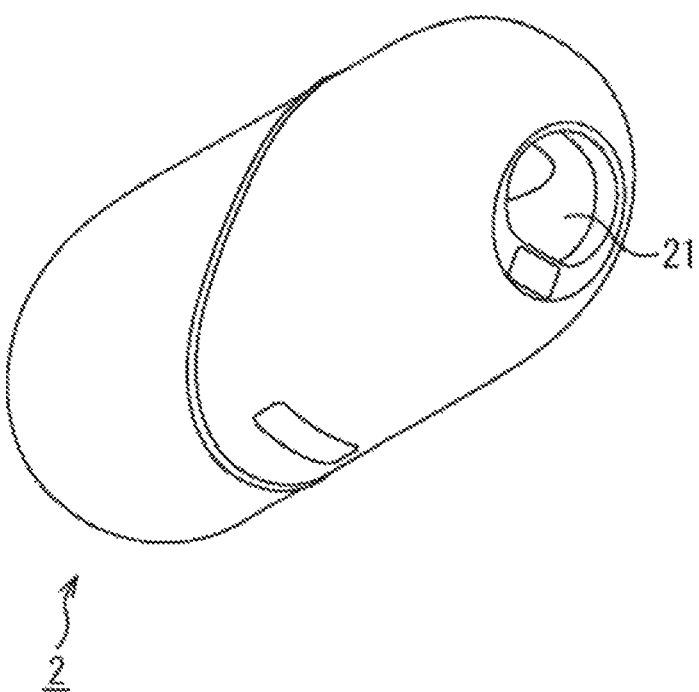

FIGS. 2A and 2B are diagrams illustrating an external view of the skin measurement device 2.

As illustrated in FIG. 2A, the skin measurement device 2 has a housing formed in a substantially horizontally-long elliptical shape in a side view. A flat surface is formed at a position slightly displaced from a top portion at a right end of the housing, and a hole portion 21 having a substantially circle shape is formed on this flat surface as illustrated in FIG. 2B. The skin measurement device 2 is entirely formed of a curved surface except for a periphery of the hole portion 21 of the housing thereof.

The deep inside of the hole portion 21 is provided with, for example, a light emission unit adapted to emit light toward the outside of the hole portion 21 and an imaging element adapted to receive reflection light and perform photographing. When a user measures own skin condition, photographing is performed by placing this hole portion 21 on a measurement portion.

Figure 3:
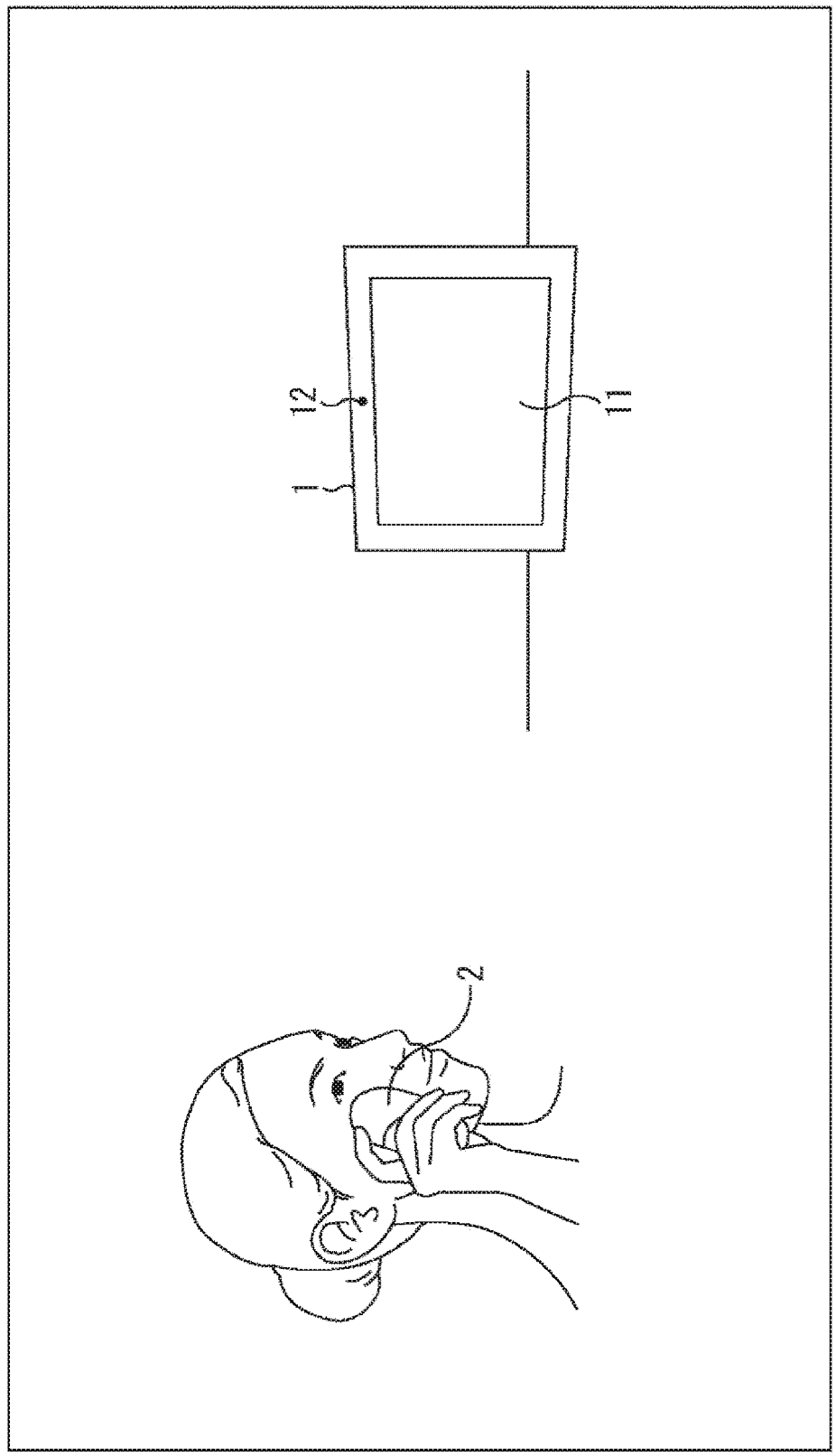
FIG. 3 is a diagram illustrating an exemplary use of the skin measurement device.

FIG. 3 is a diagram illustrating an exemplary use of the skin measurement device 2.

As illustrated in FIG. 3, the user measures the skin condition by placing the skin measurement device 2 on the own face or the like while sitting in front of the information processing device 1 located on a table or the like and viewing indication on the display 11. In this case, the information processing device 1 is set in a cradle or the lie on the table. The user can also measure the skin condition while holding the information processing device 1 with one hand and holding the skin measurement device 2 with the other hand.

The user can perform fixed-point observation on the skin condition by using the skin condition measurement system thus configured.

The information processing device 1 displays a guide on the display 11 in order that the user can photograph the same portion while using the skin measurement device 2. The user needs to periodically photograph a portion set as a fixed-point observation point by using the skin measurement device 2 in order to observe, for example, how a blemish that has appeared on a specific portion changes.

For example, while the user is using the skin measurement device 2, the information processing device 1 photographs a face of the user with the camera 12 and displays information indicating the preset fixed-point observation point in a manner superimposed on an image of the user's face. The user can photograph the fixed-point observation point by moving the hand that holds the skin measurement device 2 in accordance with the guide indicated on the display 11.

Here, the information processing device 1 is required to identify a position of a component to become a feature point such as an eye, a nose, and a mouth of the user in order to display the information indicating the fixed-point observation point in a manner superimposed on the face image. A position of a fixed-point observation point is indicated while setting a position of a feature point on the face as a reference.

Additionally, a face position and a position of the information processing device 1 are needed to have a same relation every time in order to identify the position of the feature point on the face and display the information indicating the fixed-point observation point every time at the same position. In the case where the user's face orientation in current measurement differs from that in previous measurement, the information processing device 1 cannot correctly recognize a position to be the reference. Consequently, the fixed-point observation point cannot be correctly displayed.

The information processing device 1 displays a guide to adjust the relation between the face position and the position of the information processing device 1 before displaying the information indicating the fixed-point observation point. The user's face is photographed after adjusting the relation between the face position and the position of the information processing device 1, and the information processing device 1 can display the information indicating the fixed-point observation point at the same position on the face image of the user every time by identifying the position of the feature point.

Since the guide is displayed on the display 11, the user can easily perform adjustment such that the relation between the face position and the position of the information processing device 1 becomes same every time. It may be difficult to fix the relation between the face position and the position of the information processing device 1 because the information processing device 1 is a portable device, but the user can easily perform position adjustment.

Also, the user can correctly photograph, with the skin measurement device 2, a portion preset as a fixed-point observation point by moving the hand in accordance with the guide displayed on the display 11. The user does not need to remember the portion subjected to fixed-point observation.

A series of processing of the information processing device 1 to make the user perform fixed-point observation will be described later with reference to a flowchart.

2. Configuration of Respective Devices

Configuration of Skin Measurement Device

Figure 4:
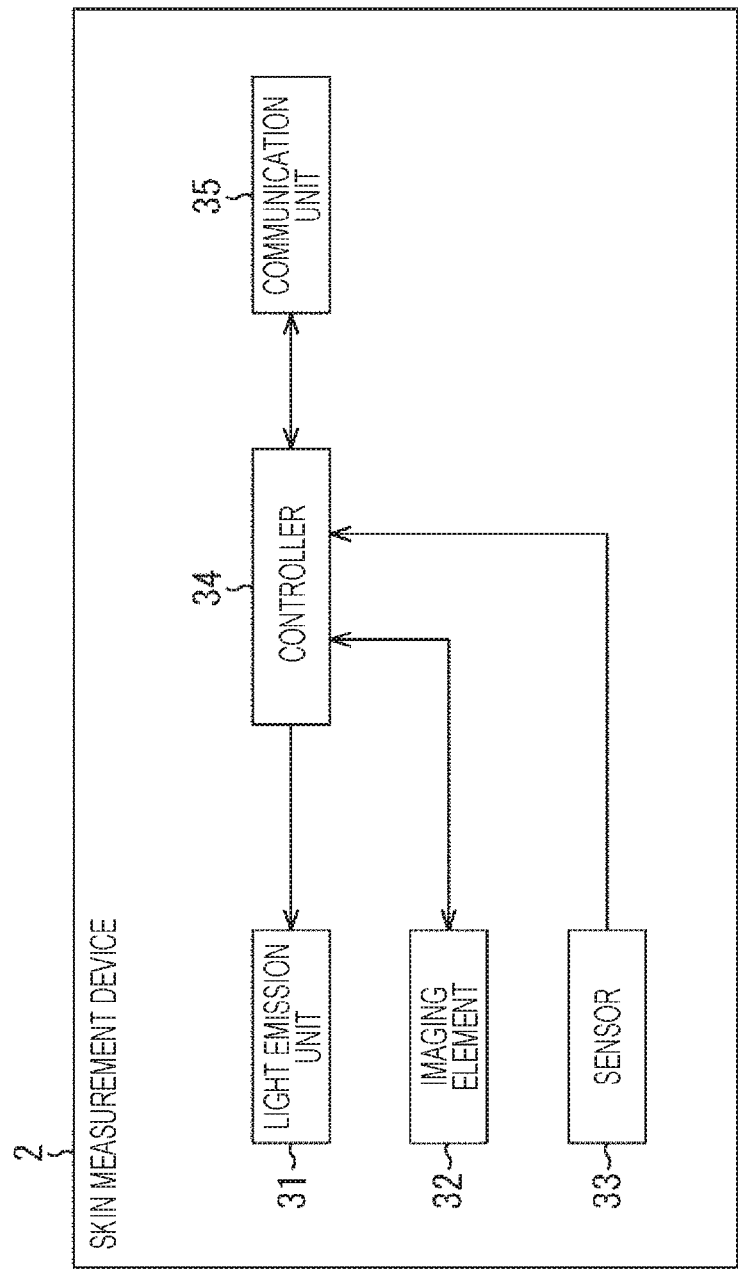
FIG. 4 is a block diagram illustrating an exemplary configuration of the skin measurement device.

FIG. 4 is a block diagram illustrating an exemplary configuration of the skin measurement device 2.

The skin measurement device 2 is formed of a light emission unit 31, an imaging element 32, a sensor 33, a controller 34, and a communication unit 35.

The light emission unit 31 emits visible light to skin at the time of photographing a skin image. Additionally, the light emission unit 31 emits light having a predetermined wavelength used to measure melanin content.

The imaging element 32 is an imaging element such as a complementary metal oxide semiconductor (CMOS) image sensor. The imaging element 32 detects reflection light of the light emitted by the light emission unit 31 and performs photoelectric conversion and the like. The imaging element 32 outputs, to the controller 34, skin image data obtained by performing photoelectric conversion and the like.

The sensor 33 includes various kinds of sensors such as a sensor to measure a skin temperature. The sensor 33 outputs, to the controller 34, sensor data indicating a measurement result.

The controller 34 communicates with the information processing device 1 via the communication unit 35, and controls the respective units of the skin measurement device 2 in accordance with control by the information processing device 1. The controller 34 transmits the skin image data supplied from the imaging element 32 and the sensor data supplied from the sensor 33 to the information processing device 1 from the communication unit 35.

The communication unit 35 is a communication module having a prescribed standard such as a wireless LAN. The communication unit 35 communicates with the information processing device 1. The communication unit 35 outputs information transmitted from the information processing device 1 to the controller 34, and transmits information supplied from the controller 34 to the information processing device 1.

Configuration of Information Processing Device

Figure 5:
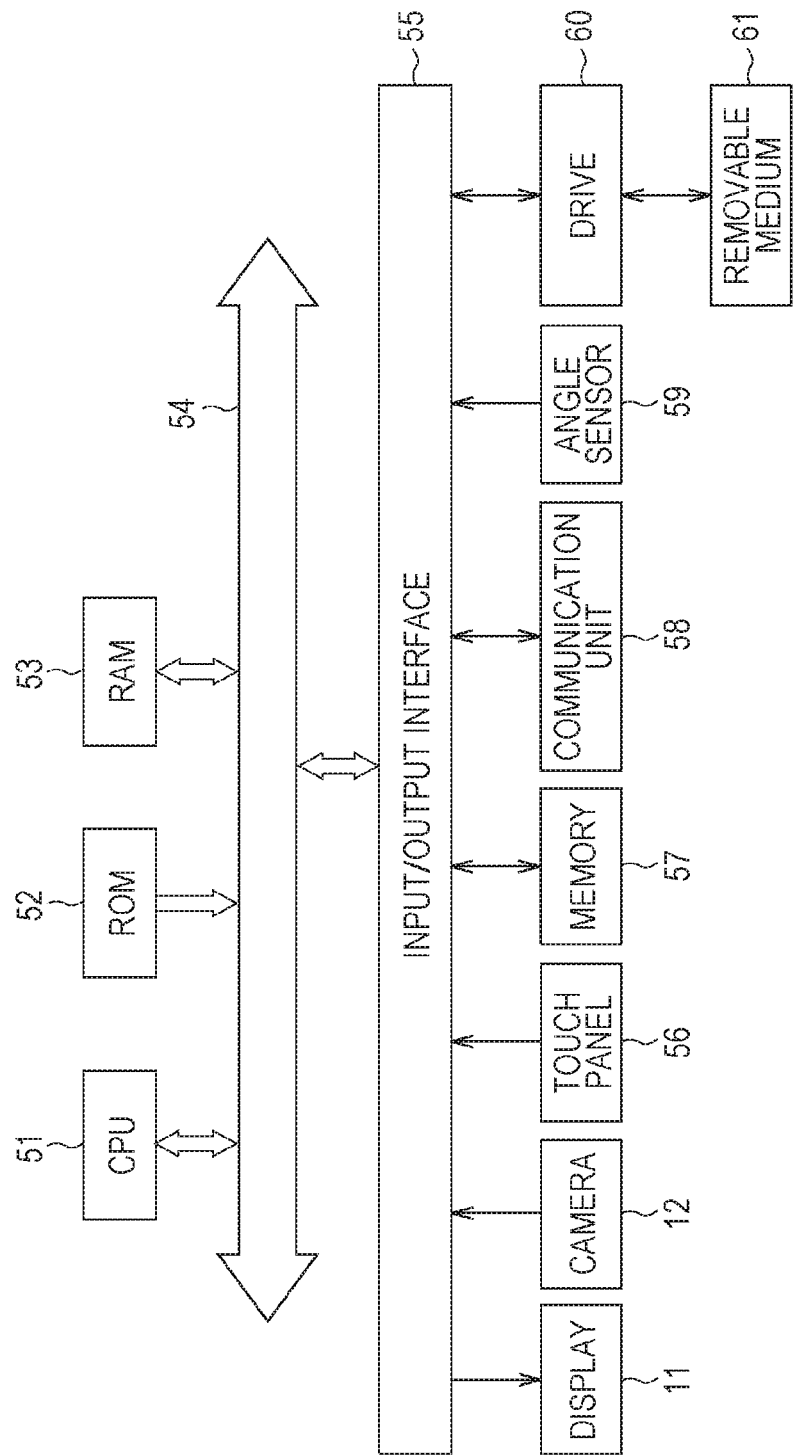
FIG. 5 is a block diagram illustrating an exemplary hardware configuration of an information processing device.

FIG. 5 is a block diagram illustrating an exemplary hardware configuration of the information processing device 1. A component same as the above-described component will be denoted by a same reference sign. Repetition of the same description will be suitably omitted.

A central processing unit (CPU) 51, a read only memory (ROM) 52, and a random access memory (RAM) 53 are mutually connected via a bus 54.

The input/output interface 55 is further connected to the bus 54. The display 11, the camera 12, a touch panel 56, a memory 57, a communication unit 58, an angle sensor 59, and a drive 60 are connected to the input/output interface 55.

The touch panel 56 is provided in a manner laminated on the display 11. The touch panel 56 detects operation by a user and outputs information indicating content of the operation to the CPU 51.

The memory 57 is formed of, for example, a flash memory. Every time the skin condition is measured, the memory 57 records various kinds of information such as a face image photographed by the camera 12, a skin image photographed by the skin measurement device 2, and information indicating a measurement result of the skin condition. The information recorded in the memory 57 is read by the CPU 51 as required.

The communication unit 58 is a communication module having a prescribed standard such as a wireless LAN. The communication unit 58 communicates with the skin measurement device 2. Additionally, the communication unit 58 is connected to an access point located in the vicinity of the information processing device 1 and to a public wireless line, and communicates with various kinds of devices such as a server connected via the internet.

The angle sensor 59 detects an angle of the housing of the information processing device 1 in predetermined timing such as at the time of measuring skin condition.

The drive 60 reads data recorded in a removable medium 61 and also records data in the removable medium 61. The removable medium 61 is a recording medium such as a memory card inserted into a slot provided in the information processing device 1 or a USB memory inserted into a terminal of the information processing device 1.

Figure 6:
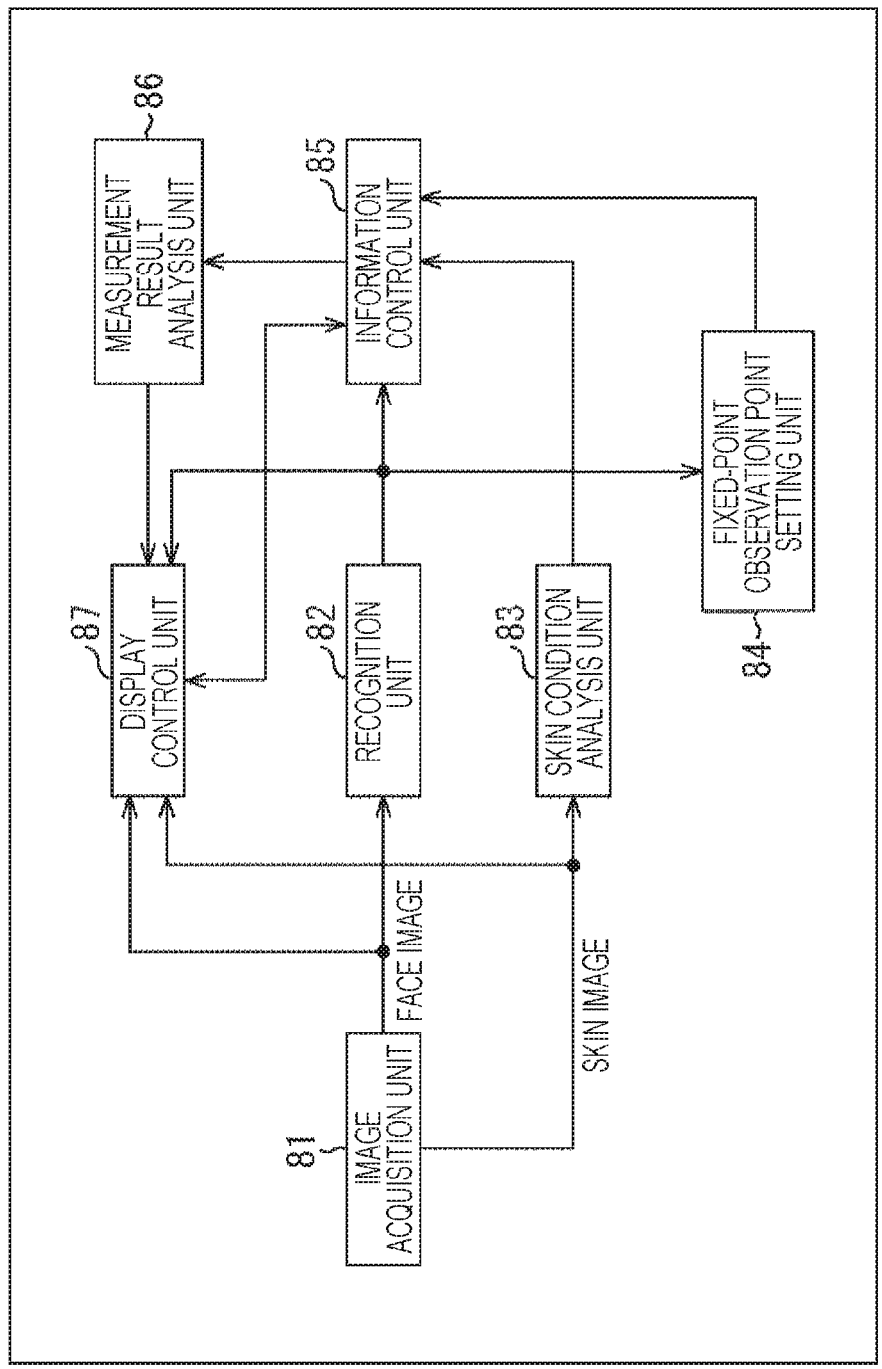
FIG. 6 is a block diagram illustrating an exemplary functional configuration of the information processing device.

FIG. 6 is a block diagram illustrating an exemplary functional configuration of the information processing device 1. At least part of functional units illustrated in FIG. 6 is implemented by a predetermined program executed by the CPU 51 of FIG. 5.

As illustrated in FIG. 6, an image acquisition unit 81, a recognition unit 82, a skin condition analysis unit 83, a fixed-point observation point setting unit 84, an information control unit 85, a measurement result analysis unit 86, and a display control unit 87 are implemented in the information processing device 1.

The image acquisition unit 81 performs photographing by controlling the camera 12. The image acquisition unit 81 acquires a face image that is a moving image or a still image which is obtained by performing photographing and shows a face of a user existing in front of the information processing device 1. Furthermore, the image acquisition unit 81 acquires a skin image photographed with the skin measurement device 2 and received in the communication unit 58 at the time of measuring the skin condition.

The image acquisition unit 81 outputs the face image to the recognition unit 82 and the display control unit 87, and outputs the skin image to the skin condition analysis unit 83 and the display control unit 87. Sensor data transmitted from the skin measurement device 2 is also acquired by the image acquisition unit 81, and supplied to the skin condition analysis unit 83.

The recognition unit 82 analyzes the face image supplied from the image acquisition unit 81, and recognizes a feature point on the face of the user. Recognition of the feature point is performed by matching feature data prepared in advance with feature data extracted from each region of the face image. The recognition unit 82 identifies a position of each feature point on the face image.

In the following, a description will be provided for a case where processing is performed by setting, as feature points, three points including both eyes and a mouth shown on the face image, but the processing may also be performed while including other components such as a nose, eyebrows, and ears as the feature points. The number of components used as feature points and combination thereof are optional.

Additionally, the recognition unit 82 identifies a distance from the information processing device 1 to each feature point. The recognition unit 82 functions as a distance sensor adapted to measure a distance to a feature point shown on a face image.

A position of a feature point on the face in a photographing space (3D space) can be identified based on the position of the feature point on the face image and the distance to each feature point. The recognition unit 82 functions to recognize a three-dimensional shape of the user's face. The recognition unit 82 outputs information including the position and the distance of the feature point together with the face image. The information output from the recognition unit 82 is supplied to the fixed-point observation point setting unit 84, information control unit 85, and display control unit 87.

The skin condition analysis unit 83 analyzes a skin image supplied from the image acquisition unit 81 and measures skin condition. The sensor data detected by the skin measurement device 2 is also suitably used to measure the skin condition. For example, respective items including a skin color, texture, moisture content, oil content, pore condition, melanin content, a blood flow rate, and a skin temperature are measured. The skin condition analysis unit 83 outputs skin condition information that is the information indicating the measured skin condition to the information control unit 85 together with the skin image.

The fixed-point observation point setting unit 84 sets a fixed-point observation point at the time of initial setting. The user needs to set the fixed-point observation point by the initial setting before performing fixed-point observation on the skin condition.

For example, the fixed-point observation point setting unit 84 identifies positions of the user's cheek, forehead, and mouth area on the basis of the positions of the feature points identified by the recognition unit 82, and sets these positions as fixed-point observation points. Additionally, the fixed-point observation point setting unit 84 sets a portion designated by the user as a fixed-point observation point. Designation of the fixed-point observation point is performed by, for example, directly touching a position on the face image displayed on the display 11 with a finger.

As described later, the user can also optionally designate a desired position as a fixed-point observation point after designating a position of a feature point. The position of the fixed-point observation point optionally designated is represented while setting, as references, the positions of the feature points designated by the user. The fixed-point observation point setting unit 84 outputs positional information of the fixed-point observation point to the information control unit 85.

The information control unit 85 causes the memory 57 to record: the information including the position and the distance of the feature point recognized by the recognition unit 82; and the face image. Furthermore, the information control unit 85 causes the memory 57 to record: skin condition information measured by the skin condition analysis unit 83; and the skin image. Such information is recorded in the memory 57 in a manner correlated to information such as measurement date and time. The information control unit 85 causes the memory 57 to record the positional information of the fixed-point observation point set by the fixed-point observation point setting unit 84.

The information control unit 85 reads various kinds of information recorded in the memory 57 as required, and outputs the same to the measurement result analysis unit 86 and the display control unit 87. For example, the information control unit 85 outputs skin condition information obtained in each measurement to the measurement result analysis unit 86 at the time of displaying a result of fixed-point observation.

The measurement result analysis unit 86 analyzes change of the skin condition at the fixed-point observation point on the basis of the skin condition information supplied from the information control unit 85. The measurement result analysis unit 86 outputs an analysis result to the display control unit 87.

The display control unit 87 displays, on the display 11, a screen at the time of initial setting and various kinds of information such as the analysis result by the measurement result analysis unit 86.

3. Operation of Information Processing Device

Here, processing of the information processing device 1 having the above-described configuration will be described.

Initial Setting Processing 1

First, initial setting processing will be described with reference to a flowchart of FIG. 7.

As described above, the initial setting processing is the processing to set a fixed-point observation point. Setting of a fixed-point observation point includes: processing to set a predetermined portion as a fixed-point observation point; and processing to designate and select a desired portion on a face image by a user oneself.

Figure 7:
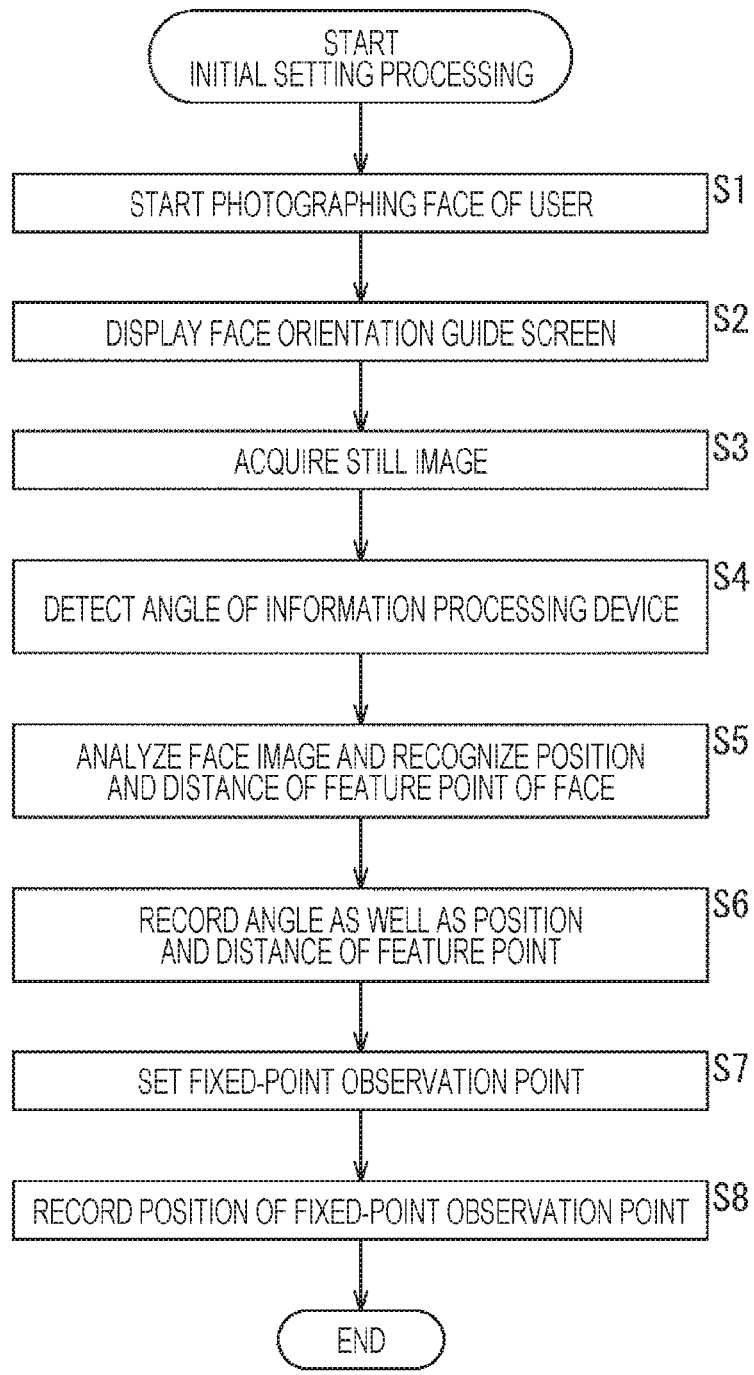
FIG. 7 is a flowchart to describe initial setting processing.

The processing in FIG. 7 is the former processing to set a predetermined portion as a fixed-point observation point. For example, the processing in FIG. 7 is started when execution of initial setting is selected from a menu screen.

In Step S1, the image acquisition unit 81 controls the camera 12 and starts photographing a face of a user. Face image data which is a moving image showing the face of the user is sequentially supplied to the recognition unit 82 and the display control unit 87.

In Step S2, the display control unit 87 displays a face orientation guide screen on the display 11.

Figure 8:
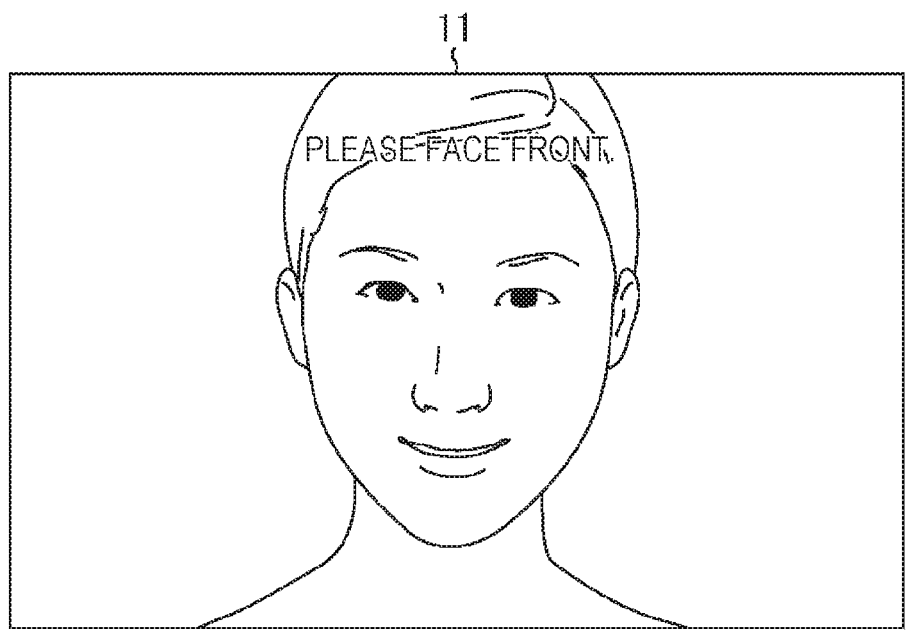
FIG. 8 is a diagram illustrating an exemplary face orientation guide screen.

FIG. 8 is a diagram illustrating an exemplary face orientation guide screen.

A face image in FIG. 8 is a moving image captured by the camera 12 and showing the face of the user who is executing the initial setting. A message to provide a guide on orienting a front side of the face toward the information processing device 1 is displayed at an upper portion of the display 11. The user orients the front side of the face toward the information processing device 1 in accordance with the guide screen in FIG. 8.

In Step S3, the image acquisition unit 81 acquires, as a still image, a predetermined frame constituting the face image photographed by the camera 12. For example, the image acquisition unit 81 acquires, as the still image, a frame when the user orients the front side of the face to the information processing device 1.

In Step S4, the angle sensor 59 detects an angle of the information processing device 1. The angle information detected by the angle sensor 59 is supplied to the information control unit 85.

In Step S5, the recognition unit 82 analyzes the face image acquired as the still image, and recognizes feature points of the face, such as three points of both eyes and the mouth. Furthermore, the recognition unit 82 identifies positions of the respective feature points on the face image as well as distances to the respective feature points from the information processing device 1. Information including the positions and the distances of the feature points identified by the recognition unit 82 is supplied to the fixed-point observation point setting unit 84 and the information control unit 85 together with the face image.

In Step S6, the information control unit 85 causes the memory 57 to record: the angle information of the information processing device 1; information including the positions and the distances of the feature points; and face image. The face image recorded in the memory 57 is, for example, the still image used to recognize the feature points on the face.

In Step S7, the fixed-point observation point setting unit 84 sets, as fixed-point observation points, the cheek, forehead, and mouth area of the user. The positions of the respective fixed-point observation points are identified while setting the positions of the feature points as the references. In this example, it is predetermined to set each of the cheek, forehead, and mouth area as the fixed-point observation point.

Thus, the user can automatically set a plurality of portions as the fixed-point observation points. The user may also be able to select a portion to be a fixed-point observation point from among predetermined positions such as the cheek, forehead, mouth area, and eye area.

Figure 9:
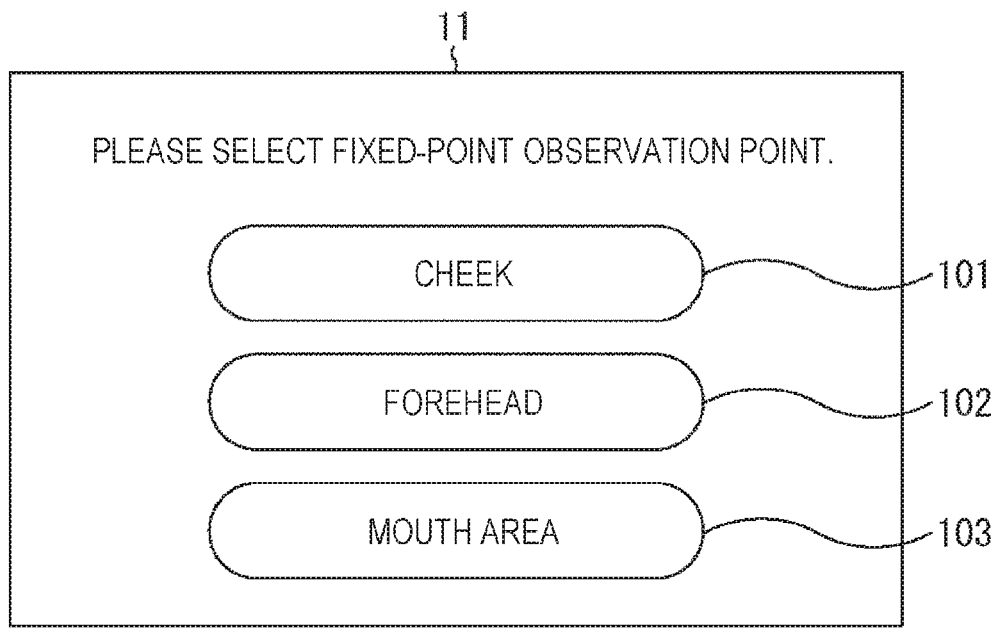
FIG. 9 is a diagram illustrating an exemplary selection screen for a fixed-point observation point.

FIG. 9 is a diagram illustrating an exemplary selection screen for a fixed-point observation point.

A message to suggest selection of a portion to be fixed-point observation point is displayed at an upper portion of the selection screen in FIG. 9. Buttons 101 to 103 are displayed under the message. The buttons 101 to 103 are buttons adapted to be selected when the cheek, forehead, and mouth area are respectively set as the fixed-point observation points.

Setting of a fixed-point observation point by using the selection screen in FIG. 9 differs from later-described processing in which a user sets a fixed-point observation point by optionally designating a desired portion without positional limitation.

In Step S8, the information control unit 85 causes the memory 57 to record information indicating a position of the fixed-point observation point. The initial setting processing is finished with the above-described processing.

FIG. 10 is a diagram illustrating exemplary setting information.

The setting information is information to be recorded in the memory 57 by executing the initial setting processing. In the case where a plurality of users uses the information processing device 1, the setting information for each of the user is recorded in the memory 57.

As illustrated in FIG. 10, the setting information includes angle information of the information processing device 1 at the time of initial setting. Additionally, the setting information includes: positional information of respective feature points 1 to 3 on a face image; and distance information from the information processing device 1 to the respective feature points 1 to 3. In the example of FIG. 10, the feature points 1 to 3 are a left eye, a right eye, and a mouth.

The setting information includes positional information of the respective fixed-point observation points 1 to 3 on the face image. The distance information from the information processing device 1 to the fixed-point observation points 1 to 3 may also be recorded. In the above-described case, the fixed-point observation points 1 to 3 are the cheek, forehead, and mouth area.

Initial Setting Processing 2

Next, another initial setting processing will be described with reference to a flowchart of FIG. 11.

Figure 11:
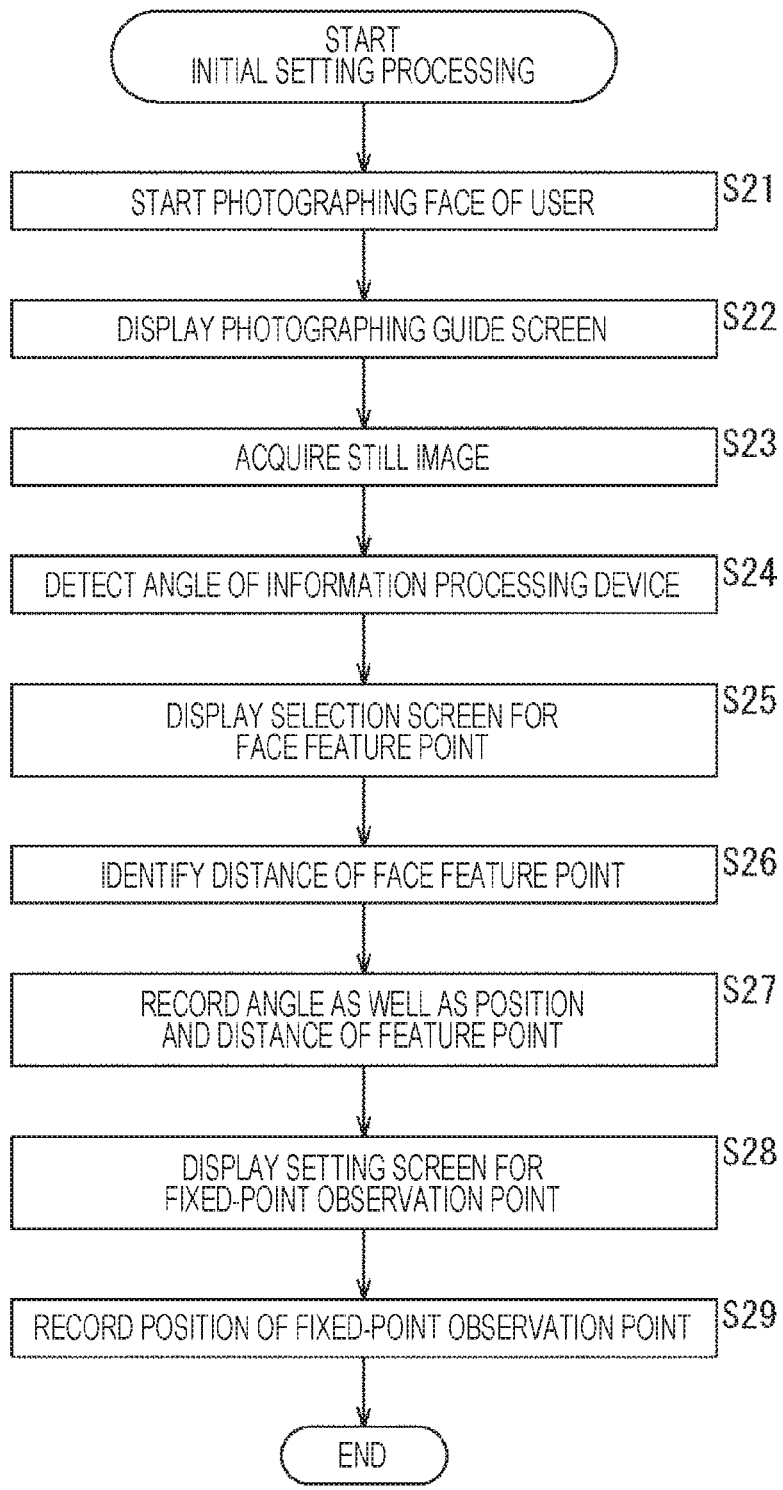
FIG. 11 is a flowchart to describe another initial setting processing.

The processing in FIG. 11 is processing in which a user independently sets a fixed-point observation point by designating an optional portion on a face image. The processing in FIG. 11 is the processing basically similar to the processing described with reference to FIG. 7 except that designation of a feature point and designation of a portion to be a fixed-point observation point are performed by the user.

In Step S21, the image acquisition unit 81 controls the camera 12 and starts photographing a face of a user. Face image data that is a moving image showing the face of the user is supplied to the recognition unit 82 and the display control unit 87.

In Step S22, the display control unit 87 displays a photographing guide screen on the display 11.

Figure 12:
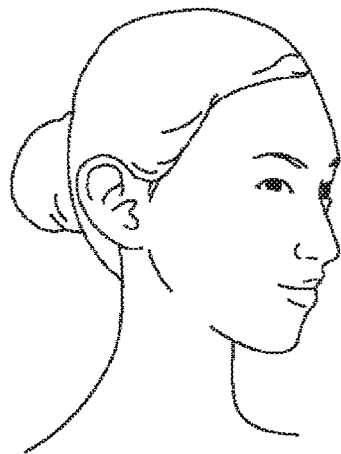
FIG. 12 is a diagram illustrating an exemplary photographing guide screen.

FIG. 12 is a diagram illustrating an exemplary photographing guide screen.

A face image in FIG. 12 is a moving image captured by the camera 12 and showing the face of the user who is executing the initial setting. A message to provide a guide on photographing in a desired orientation is displayed at an upper portion of the display 11. In the example of FIG. 12, the face of the user is not oriented toward the information processing device 1 (camera 12).

The user adjusts the face orientation in accordance with the guide screen of FIG. 12 such that a portion desired to be a fixed-point observation point is shown. A button 104 adapted to be operated at the time of determining the face orientation is displayed on a right lower portion of the guide screen.

In Step S23, the image acquisition unit 81 acquires, as a still image, a frame which constitutes a face image photographed by the camera 12 and corresponds to timing when the button 104 of FIG. 12 is operated. The still image shows the user's face oriented in a desired direction. The image acquisition unit 81 outputs, as a face image, the acquired still image to the recognition unit 82 and the display control unit 87.

In Step S24, the angle sensor 59 detects an angle of the information processing device 1. The angle information detected by the angle sensor 59 is supplied to the information control unit 85.

In Step S25, the display control unit 87 displays a feature point selection screen on the display 11.

Figure 13:
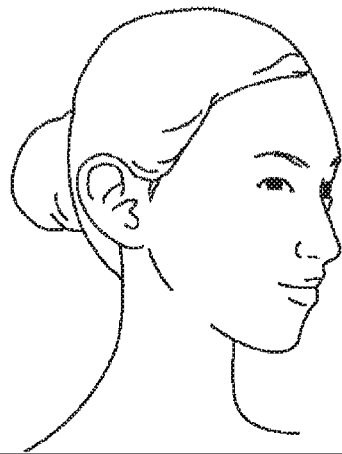
FIG. 13 is a diagram illustrating an exemplary feature point selection screen.

FIG. 13 is a diagram illustrating an exemplary feature point selection screen.

The face image in FIG. 13 is, for example, a still image acquired by the image acquisition unit 81. A message to provide a guide on designating positions of the eyes and mouth to be the feature points is displayed at the upper portion of the display 11.

The user performs designation by directly touching positions of the both eyes and mouth on the own face image in accordance with the selection screen in FIG. 13. The touch panel 56 detects the positions designated by the user. Information indicating the positions designated by the user is supplied to the recognition unit 82 as positional information of the feature points.

In Step S26, the recognition unit 82 analyzes the face image, and identifies distances to the feature points from the information processing device 1. Here, a subject shown at the positions designated by the user are processed as the feature points. The information including the positions of the feature points and the distances of the feature points identified by the recognition unit 82 is supplied the fixed-point observation point setting unit 84 and the information control unit 85 together with the face image.

In Step S27, the information control unit 85 causes the memory 57 to record: angle information of the information processing device 1; information including the positions and the distances of the feature points; and face image.

In Step S28, the display control unit 87 displays a setting screen for a fixed-point observation point on the display 11.

Figure 14:
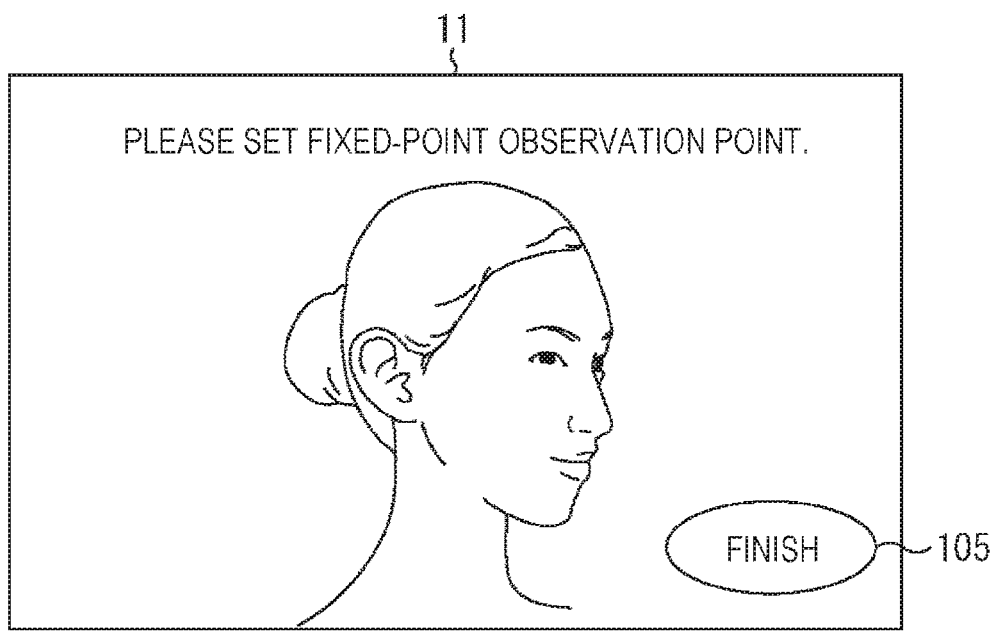
FIG. 14 is a diagram illustrating an exemplary setting screen for a fixed-point observation point.

FIG. 14 is a diagram illustrating an exemplary setting screen for a fixed-point observation point.

A face image in FIG. 14 is, for example, a still image acquired by the image acquisition unit 81. A message to provide a guide on designating a fixed-point observation point is displayed at an upper portion of the display 11. A button 105 to be operated at the time of finishing the fixed-point observation point setting is displayed at a lower portion of the setting screen.

The user performs designation by directly touching any position on the own face image in accordance with the screen of FIG. 14. The user can designate a desired position as the fixed-point observation point. Information indicating the position designated by the user is acquired by the fixed-point observation point setting unit 84.

The fixed-point observation point setting unit 84 sets the position designated by the user as the fixed-point observation point, and supplies the information indicating the position of the fixed-point observation point to the information control unit 85. The position of the fixed-point observation point is represented while setting, as a reference, the positions of the feature points designated by the user.

In Step S29, the information control unit 85 causes the memory 57 to record the information indicating the position of the fixed-point observation point. The initial setting processing is finished with the above-described processing. The setting information in FIG. 10 is recorded in the memory 57.

Measurement Processing

Next, measurement processing will be described with reference to a flowchart of FIG. 15.

Figure 15:
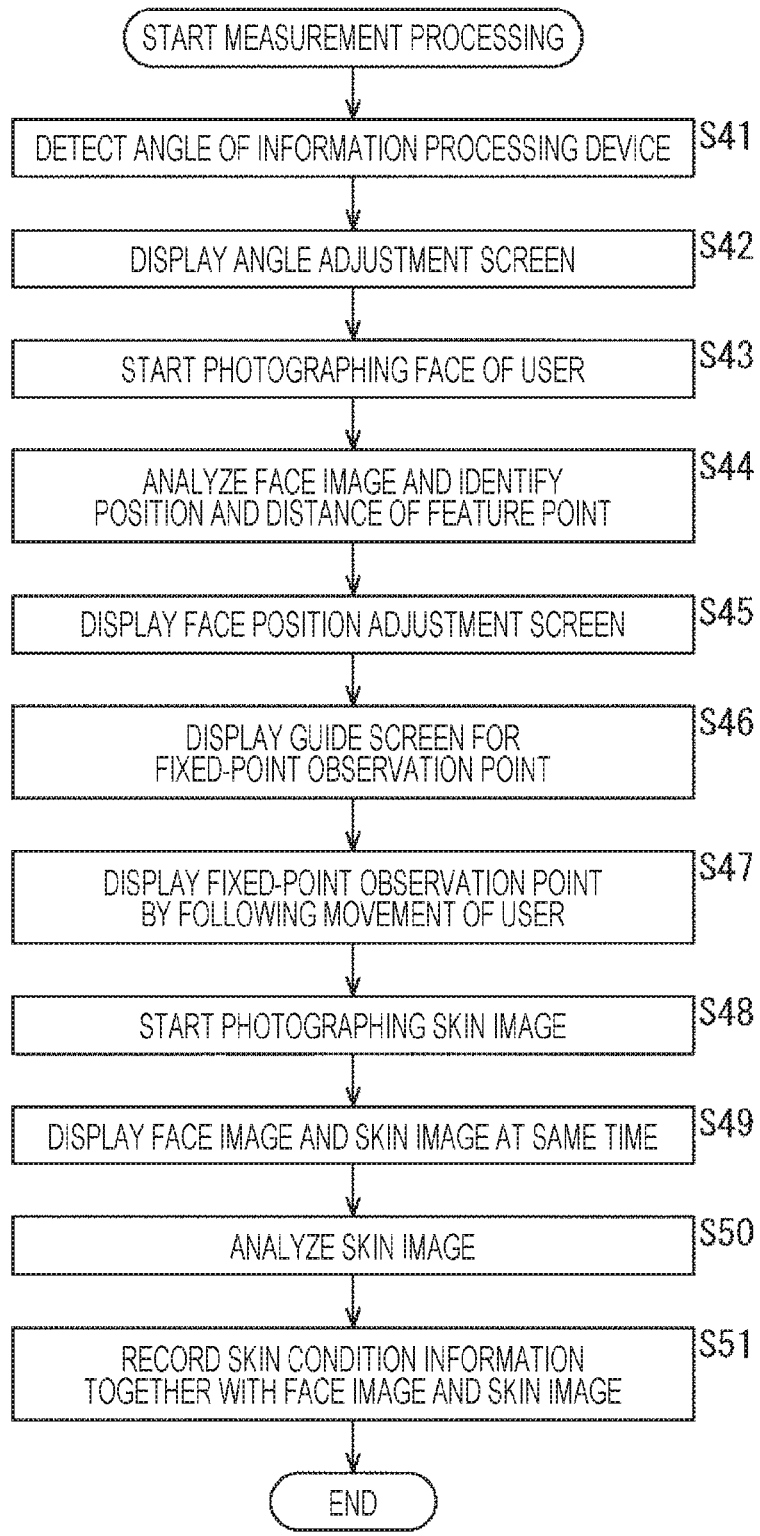
FIG. 15 is a flowchart to describe measurement processing.

The processing in FIG. 15 is processing to actually measure skin condition at a fixed-point observation point. The processing in FIG. 15 is performed after having performed the initial setting processing in FIG. 7 or FIG. 11.

In Step S41, the angle sensor 59 detects an angle of the information processing device 1. The angle information detected by the angle sensor 59 is supplied to the display control unit 87.

In Step S42, in the case where the angle detected by the angle sensor 59 differs from an angle at the time of initial setting, the display control unit 87 displays an angle adjustment screen on the display 11. The display control unit 87 controls display of the adjustment screen by comparing the angle detected by the angle sensor 59 with the angle at the time of initial setting represented based on the setting information recorded in the memory 57.

Figure 16:
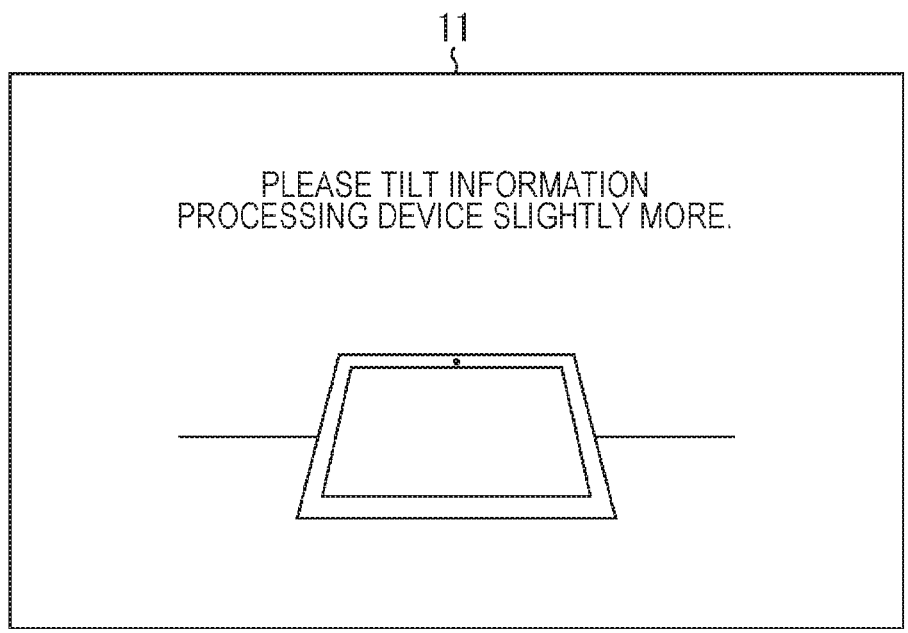
FIG. 16 is a diagram illustrating an exemplary angle adjustment screen.

FIG. 16 is a diagram illustrating an exemplary angle adjustment screen.

A message to provide a guide on tilting the information processing device 1 from a current state is displayed at an upper portion of the adjustment screen. Thus, the message to suggest adjustment of the angle of the information processing device 1 to an angle same as the angle at the time of initial setting is displayed on the adjustment screen.

The user adjusts the angle of the information processing device 1 located in front in accordance with the screen in FIG. 16. Consequently, the angle of the information processing device 1 is adjusted to the angle same as the angle at the time of initial setting.

In Step S43, the image acquisition unit 81 controls the camera 12 and starts photographing a face of a user. Face image data that is a moving image showing the face of the user is supplied to the recognition unit 82 and the display control unit 87.

In Step S44, the recognition unit 82 analyzes the face image, and identifies a position of a feature point on the face image and a distance to each feature point from the information processing device 1. Identification of the position and the distance of the feature point is repeatedly performed. The information including the positions and the distances of the feature points is supplied to the display control unit 87.

In Step S45, the display control unit 87 displays a face position adjustment screen on the display 11. The adjustment screen is displayed by using the information including the positions and the distances of the feature points at the time of initial setting included in the setting information.

Figure 17:
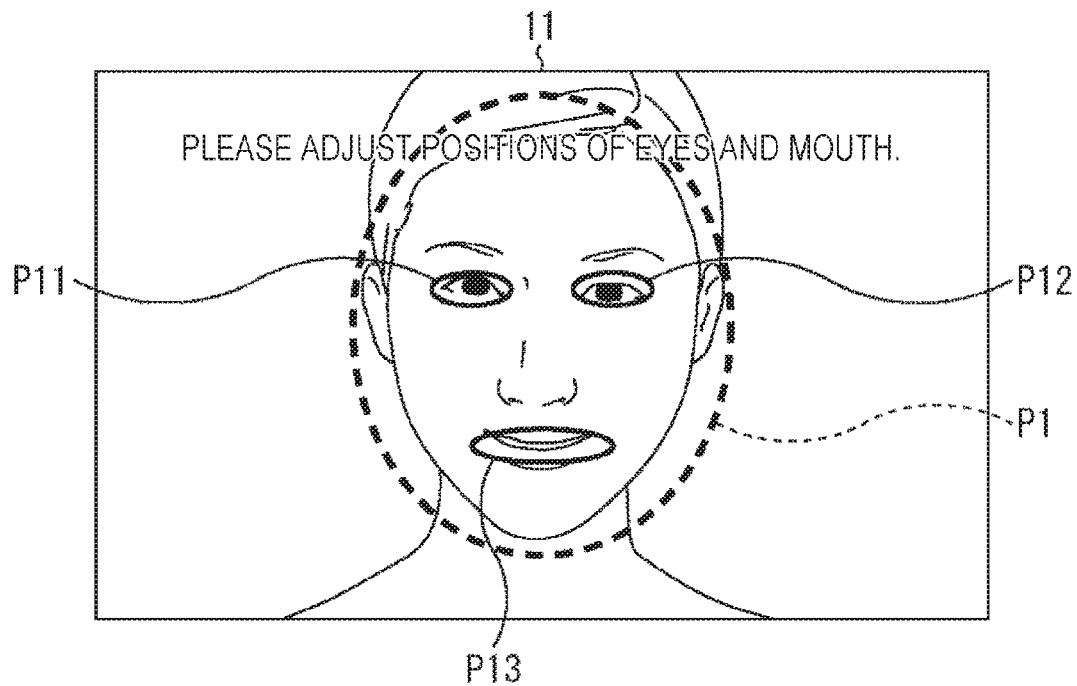
FIG. 17 is a diagram illustrating an exemplary face position adjustment screen.

FIG. 17 is a diagram illustrating an exemplary face position adjustment screen.

A face image in FIG. 17 is a moving image captured by the camera 12. A message to provide a guide on adjusting a face position such that positions of eyes and mouth conform to markers is displayed at an upper portion of the adjustment screen.

An image P1 that is a vertically-long elliptic image indicated by a dotted line is displayed in a manner superimposed on the face image at a nearly center of the adjustment screen. The image P1 is an image to be a target range within which the face is fitted.

Images P11 to P13 to be markers are displayed on an inner side of the image P1 in a manner superimposed on the face image. The image P11 is displayed on the basis of the right eye position identified at the time of initial setting. The image P12 is displayed on the basis of the left eye position identified at the time of initial setting. The image P13 is displayed on the basis of the mouth position identified at the time of initial setting.

A user adjusts orientation and distance of the face in accordance with the screen of FIG. 17 such that three points of both eyes and mouth are fitted inside the images P11 to P13 respectively. Consequently, a positional relation between the face and the information processing device 1 comes to have the same relation at the time of initial setting.

Figure 18:
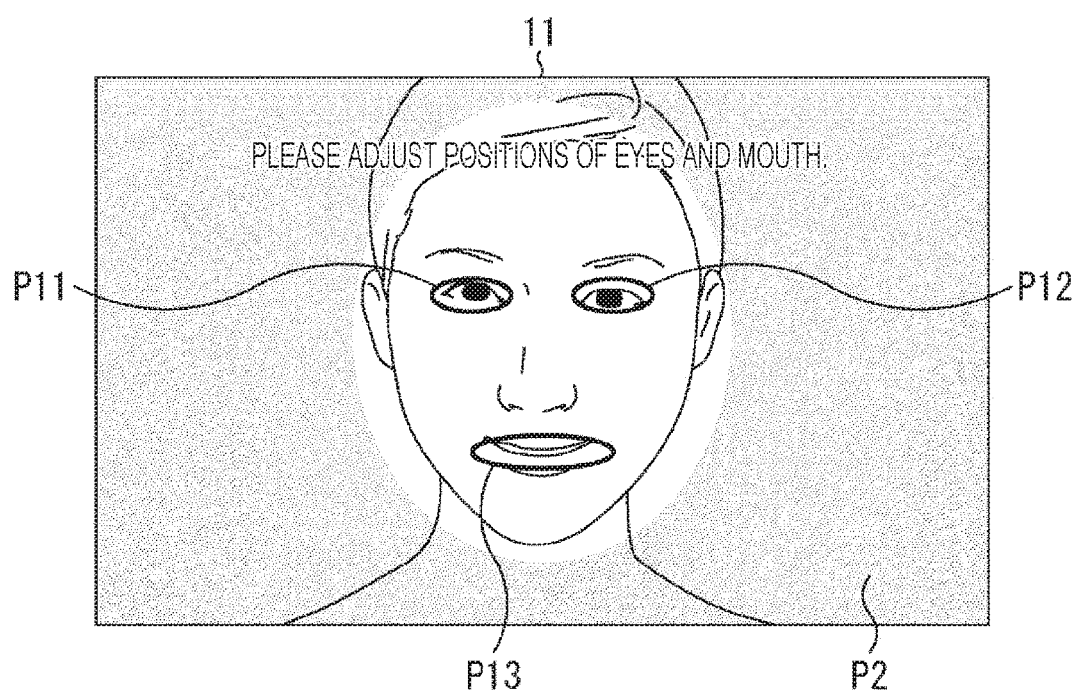
FIG. 18 is a diagram illustrating another exemplary face position adjustment screen.

FIG. 18 is a diagram illustrating another exemplary face position adjustment screen.

An image P2 that is an image to gray out a range other than a range surrounded by the image P1 is displayed on the adjustment screen of FIG. 18 instead of the image P1 in FIG. 17. Since the portion other than the vicinity of the face in the center is grayed out, the user can concentrate on adjustment of the face position.

In Step S46, the display control unit 87 displays a guide screen for a fixed-point observation point on the display 11. The guide screen is displayed by using positional information of the fixed-point observation point included in the setting information.

Figure 19:
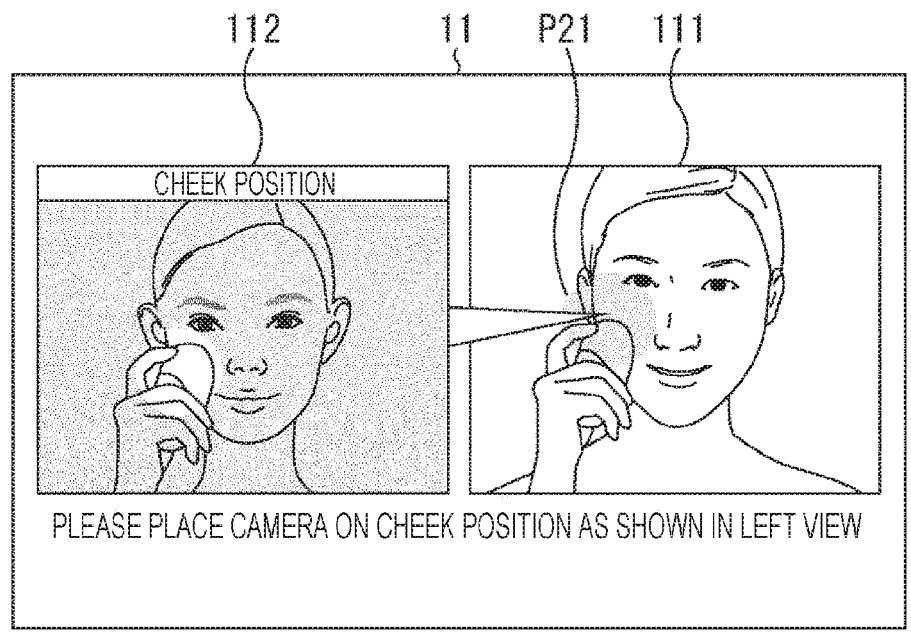
FIG. 19 is a diagram illustrating an exemplary guide screen for a fixed-point observation point.

FIG. 19 is a diagram illustrating an exemplary guide screen for a fixed-point observation point.

The guide screen in FIG. 19 is formed by arranging a face image 111 and a balloon 112 side by side.

The face image 111 is a moving image which is photographed by the camera 12 and shows the face of the user. An image P21 indicating a fixed-point observation point is displayed in a manner superimposed on the face image 111.

In the example of FIG. 19, the image P21 is displayed close to the right cheek of the user. The image P21 is a round image of a vivid color such as red or blue. The image P21 is transparent, and a portion of the user's face is displayed under the image P21.

The display position of the image P21 is determined on the basis of the positional information of the fixed-point observation point included in the setting information. The positions of the feature points to be references are identified by the recognition unit 82 by analyzing the face image being photographed.

Since the positions of the feature points are identified by analyzing the face image being photographed and the fixed-point observation point is displayed while setting these positions as the references, the display control unit 87 can constantly display the fixed-point observation point at the same position on the face image.

An illustration that indicates a state of a person who is placing the skin measurement device on the right cheek is displayed in the balloon 112. An origin of the balloon 112 is located at a position of the image P21 displayed on the face image 111. The illustration of the balloon 112 is displayed in a manner graying out a portion other than a range corresponding to the fixed-point observation point.

A message to provide a guide on moving the skin measurement device 2 in the same manner as the person displayed in the balloon 112 is displayed below the face image 111 and the balloon 112.

The user places the skin measurement device 2 held with, for example, the right hand on the right cheek in accordance with FIG. 19, and photographs skin around the right cheek that has been set as the fixed-point observation point.

Figure 20:
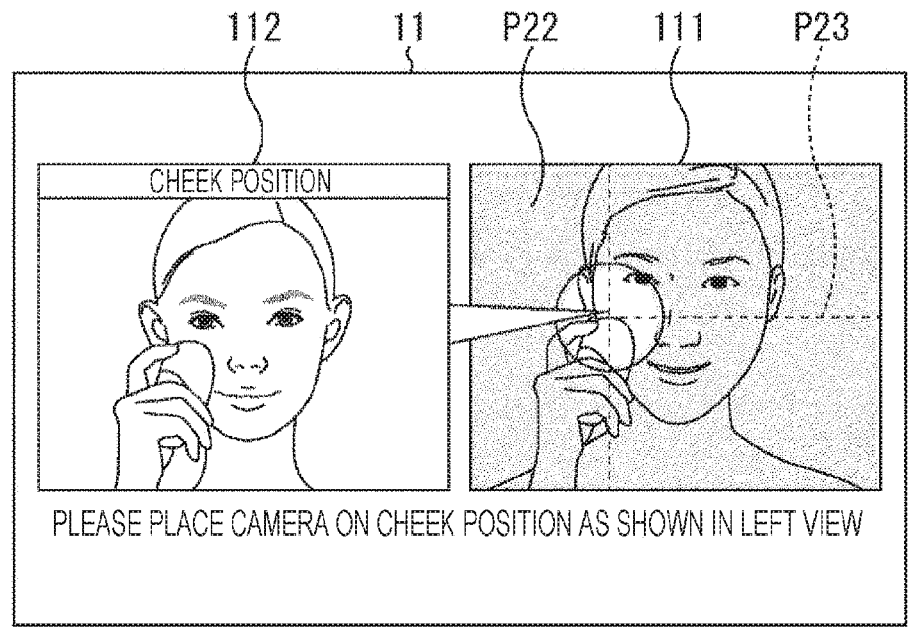
FIG. 20 is a diagram illustrating another exemplary guide screen for a fixed-point observation point.

FIG. 20 is a diagram illustrating another exemplary guide screen for a fixed-point observation point.

Constituents in the guide screen in FIG. 20 are the same as those in FIG. 19. An image P22 that is an image to gray out a range other than a fixed-point observation point is displayed in a manner superimposed on a face image 111 of the FIG. 20. Additionally, an image P23 that is a cross-shaped image crossing at the fixed-point observation point is displayed. An illustration that indicates a state of a person who is placing the skin measurement device on the right cheek is displayed in the balloon 112.

In Step S47 of FIG. 15, the display control unit 87 displays the fixed-point observation point in accordance with movement of the user. In the case where the user changes orientation of the face, positions of the feature points as changed are identified by the recognition unit 82. The display control unit 87 determines a position of a fixed-point observation point while setting the changed positions of the feature points as the references, and displays the image P21 or the like indicating the fixed-point observation point at the determined position.

In Step S48, the image acquisition unit 81 controls the skin measurement device 2 and starts photographing of a skin image. Photographing of the skin image is repeatedly performed. The skin image photographed by the skin measurement device 2 is acquired by the image acquisition unit 81, and supplied to the skin condition analysis unit 83 and the display control unit 87.

In the case where a position of the skin measurement device 2 can be recognized on the basis of the face image photographed by the camera 12, photographing of a skin image may be started when the user places the skin measurement device 2 on the fixed-point observation point.

In Step S49, the display control unit 87 displays, on the display 11, the face image photographed by the camera 12 and the skin image photographed by the skin measurement device 2 at the same time.

Figure 21:
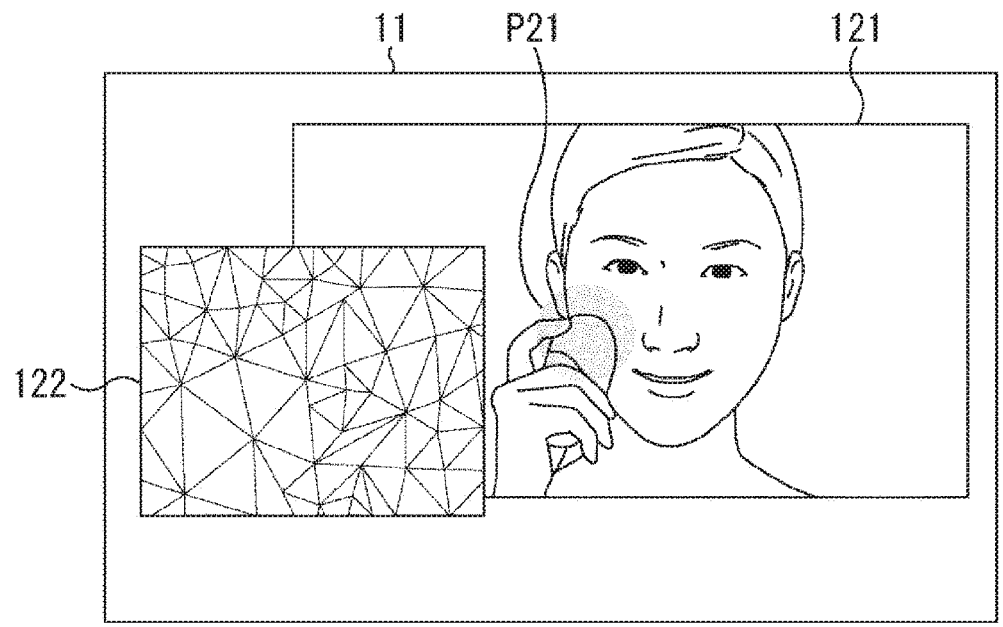
FIG. 21 is a diagram illustrating an exemplary display screen.

FIG. 21 is a diagram illustrating an exemplary display screen.

A display screen in FIG. 21 is formed of a face image 121 and a skin image 122. The skin image 122 and the face image 121 are arranged in a manner partly superimposed.

The face image 121 is a moving image photographed by the camera 12. The image P21 indicating the fixed-point observation point is displayed in a manner superimposed on the face image 121. The skin image 122 is a skin image of the cheek photographed by the skin measurement device 2.

Thus, since the skin image and the face image displaying the fixed-point observation point are displayed side by side, the user can intuitively recognize which portion of the skin is photographed to obtain the skin image. Additionally, the user can confirm, in detail, makeup condition of each portion.

Instead of displaying a moving image showing the face of the user and a moving image showing magnified skin, respective still images thereof may also be displayed at the same time.

Figure 22:
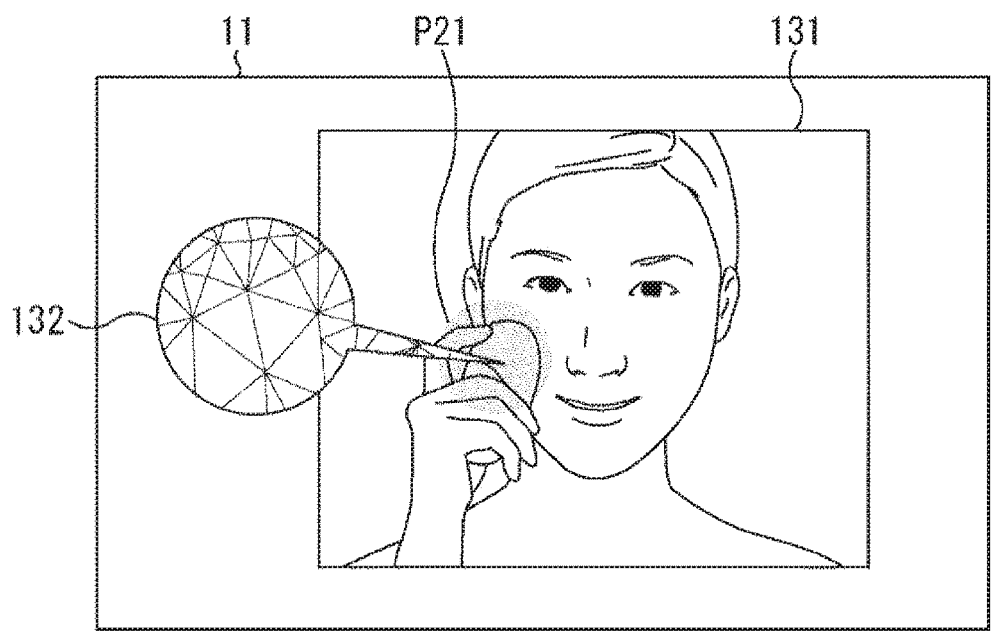
FIG. 22 is a diagram illustrating another exemplary display screen.

FIG. 22 is a diagram illustrating another exemplary display screen.

A display screen in FIG. 22 is formed of a face image 131 and a skin image P132 trimmed in a balloon shape. An origin of the skin image P132 is a position of an image P21 which is displayed in a manner superimposed on the face image 131 and indicates the fixed-point observation point.

The user can also intuitively recognize, from such a display, which portion of the skin is photographed to obtain the skin image.

In Step S50 of FIG. 15, the skin condition analysis unit 83 analyzes a predetermined frame out of the skin image supplied from the image acquisition unit 81, and measures skin condition. The skin condition analysis unit 83 outputs, to the information control unit 85, skin condition information indicating the skin condition together with the skin image.

In Step S51, the information control unit 85 causes the memory 57 to record the skin condition information together with the face image and the skin image. The processing in Steps from S46 to S51 is performed for each fixed-point observation point. The face image recorded in the memory 57 is, for example, the still image used to recognize the feature points on the face. Additionally, the skin image recorded in the memory 57 is the still image used to measure the skin condition.

Figure 23:
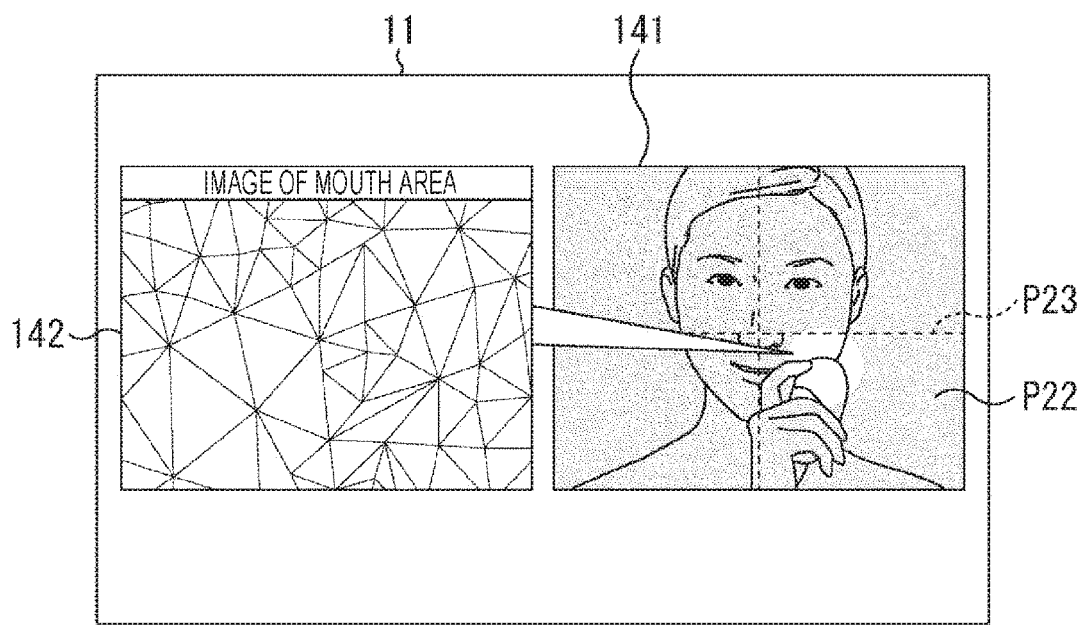
FIG. 23 is a diagram illustrating an exemplary display screen while photographing a mouth area.

FIG. 23 is a diagram illustrating an exemplary display screen while photographing the mouth area that is a fixed-point observation point.

The display screen in FIG. 23 is formed by arranging a face image 141 and a balloon 142 side by side.

The face image 141 is a moving image in which the user places the skin measurement device 2 on a mouth area that is the fixed-point observation point. An image P22 to gray out a range other than the fixed-point observation point is displayed in a manner superimposed on the face image 141. Furthermore, an image P23 that is an image of a cross-shaped dotted line crossing at the center is displayed on the face image 141.

In the balloon 142, a skin image photographed when the user places the skin measurement device 2 on the mouth area is displayed. An origin of the balloon 142 is located at the position in the mouth area on the face image 141.

Figure 24:
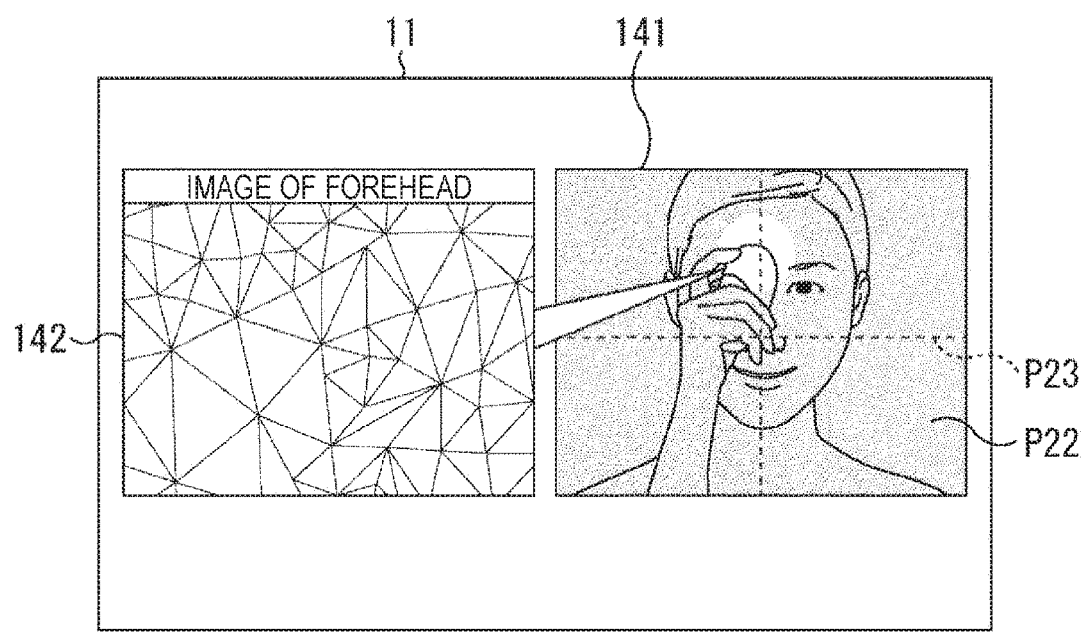
FIG. 24 is a diagram illustrating an exemplary display screen while photographing of the forehead.

FIG. 24 is a diagram illustrating an exemplary display screen while photographing the forehead that is a fixed-point observation point.

The display screen in FIG. 24 is same as the display screen in FIG. 23 except that the fixed-point observation point is different. A face image 141 in FIG. 24 is a moving image photographed when the user places the skin measurement device 2 on the forehead that is the fixed-point observation point. Furthermore, a skin image displayed in a balloon 142 is an image photographed when the user places the skin measurement device 2 on the forehead.

When skin condition measurement for all of the fixed-point observation points is completed, measurement processing ends. The above-described measurement processing is performed periodically, for example, every other day and every week.

FIG. 25 is a diagram illustrating an exemplary measurement result.

In the memory 57, a file name of a face image photographed at the time of measurement, a file name of a skin image per fixed-point observation point, and skin condition information per fixed-point observation point are recorded in a manner correlated to a measurement date and time. Respective items of the skin condition information, such as a skin color, texture, moisture content, oil content, pore condition, melanin content, a blood flow rate, and a skin temperature are indicated by, for example, values of ten grades.

The skin condition information indicated on the left side is information obtained by measurement processing performed on Jan. 1, 2014. Additionally, the skin condition information indicated on the right side is information obtained by measurement processing performed on Jan. 8, 2014.

The information processing device 1 can identify change of the skin condition at the fixed-point observation point by analyzing a result of measurement processing periodically performed as described above.

Fixed-Point Observation Result Display Processing

Next, fixed-point observation result display processing will be described with reference to a flowchart of FIG. 26.

Figure 26:
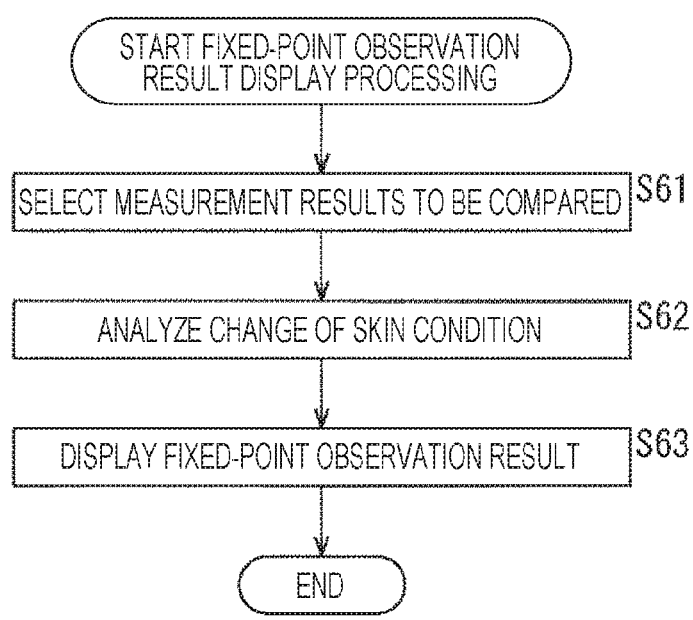
FIG. 26 is a flowchart to describe fixed-point observation result display processing.

The processing in FIG. 26 is performed after the measurement processing in FIG. 15 is performed a plurality of times and a plurality of measurement results of the skin condition is accumulated in the memory 57.

In Step S61, the measurement result analysis unit 86 selects measurement results to be compared. The measurement results to be compared are selected by a user, using a selection screen displayed on the display 11.

For example, in the case where a command is made to compare a result obtained in a previous measurement with a result obtained in measurement before the previous measurement, the measurement result analysis unit 86 controls the information control unit 85 and reads and acquires information of these measurement results from the memory 57. The information of a measurement result includes: a file name of a face image; and a file name of a skin image and skin condition information per fixed-point observation point.

In Step S62, the measurement result analysis unit 86 analyzes, per fixed-point observation point, change of the skin condition on the basis of the acquired information. The measurement result analysis unit 86 outputs, to the display control unit 87, information of an analysis result as a fixed-point observation result.

In Step S63, the display control unit 87 displays, on the display 11, a display screen of the fixed-point observation result on the basis of the information supplied from the measurement result analysis unit 86.

Figure 27:
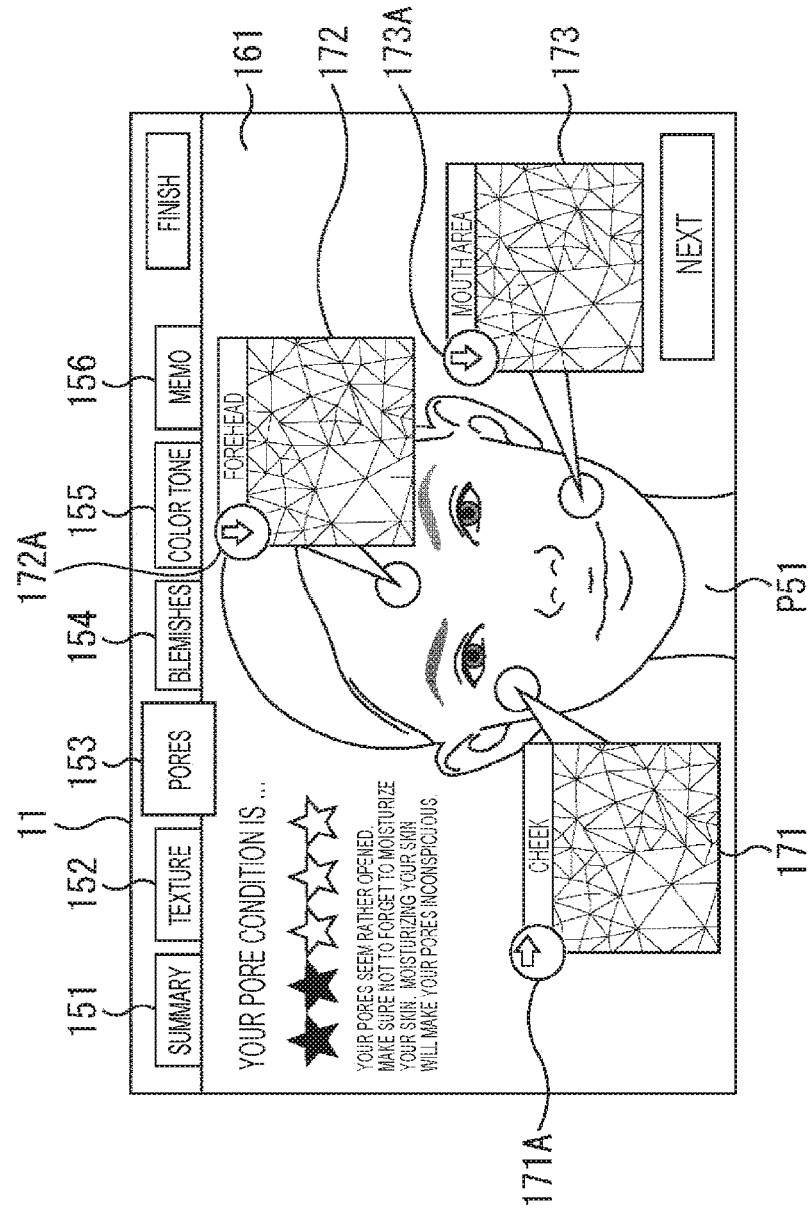
FIG. 27 is a diagram illustrating an exemplary display screen of a fixed-point observation result.

FIG. 27 is a diagram illustrating an exemplary display screen of a fixed-point observation result.

Tabs 151 to 156 are displayed in a manner laterally aligned at an upper portion of the display screen. In the respectively tabs, "summary", "texture", "pores", "blemishes", "color tone", and "memo" are displayed. The display screen in FIG. 27 is the screen in which the tab 153, namely, the tab "pore" is selected. Display in a region 161 below the tabs 151 to 156 is switched when a selected tab is changed.

An illustration P51 of a face of a person is displayed at a center of the region 161. Skin images 171 to 173 are displayed in balloons having origins at the fixed-point observation points on the illustration P51. A face image of a user who has been photographed by the camera 12 and is currently viewing a fixed-point observation result may also be displayed instead of the illustration P51. In this case, the skin images 171 to 173 are displayed while having the balloon origins at the fixed-point observation points on the face image of the user.

The skin image 171 is an image which shows, in a magnified manner, skin of the cheek which is a fixed-point observation point. For example, a skin image of a newer measurement result is displayed out of measurement results to be compared. An arrow icon 171A pointing in a lateral direction is displayed at an upper left of the skin image 171. The icon 171A indicates that there is no change in pore condition of the cheek skin.

A skin image 172 is an image which shows, in a magnified manner, skin of the forehead that is a fixed-point observation point. An arrow icon 172A pointing in a downward direction is displayed at an upper left of the skin image 172. The icon 172A indicates that the pore condition of the forehead skin is deteriorated.

A skin image 173 is an image which shows, in a magnified manner, skin of the mouth area that is a fixed-point observation point. An arrow icon 173A pointing in a downward direction is displayed at an upper left of the skin image 173. The icon 173A indicates that pore condition of skin in the mouth area is deteriorated.

Change of the pore condition is determined on the basis of pore amount information included in the skin condition information to be compared. For example, the measurement result analysis unit 86 compares values indicating the pore amounts, and in the case where the amount is reduced by a threshold or more, it is determined that the pore condition is deteriorated. Furthermore, in the case where the value indicating the pore amount is not changed, the measurement result analysis unit 86 determines that there is no change in the pore condition. In the case where the value indicating the pore amount is increased by a threshold or more, the measurement result analysis unit 86 determines that the pore condition is improved.

On the left side of the region 161, comments on the fixed-point observation result of "pore" are displayed. Content such as comments indicating a fixed-point observation result is preliminarily recorded in the memory 57. The measurement result analysis unit 86 selects content according to an analysis result from among content preliminarily recorded, and uses the content in displaying a fixed-point observation result.

The fixed-point observation result display processing is finished after confirming change of condition in each item by switching the tab.

The user can correctly and easily photograph a portion preset as a fixed-point observation point by using the skin measurement device 2 with the above-described series of processing. Furthermore, the user can make the information processing device 1 accumulate measurement results of skin condition of the same portion.

The user can confirm the fixed-point observation result on the skin condition by having the accumulated measurement results be analyzed.

4. Exemplary Classification Using Skin Condition Information

The information processing device 1 can implement various kinds of functions by using, for example, skin condition information per fixed-point observation point.

Face Image Comparing Function

A face image comparing function is a function to display, in a comparable style, face images obtained when skin condition that satisfies conditions designated by a user is measured.

Comparison display processing will be described with reference to a flowchart of FIG. 28.

In Step S101, the measurement result analysis unit 86 selects a fixed-point observation point for which skin condition information is compared. The measurement result analysis unit 86 selects, for example, a predetermined fixed-point observation point from among a plurality of fixed-point observation points such as a cheek, a forehead, a mouth area, and an eye area in accordance with user's operation on a selection screen. The fixed-point observation point set by the user is displayed on the selection screen.

In Step S102, the measurement result analysis unit 86 selects comparing conditions related to skin condition at the fixed-point observation point selected in Step S101. For example, in accordance with the user's operation, the measurement result analysis unit 86 selects conditions, such as that a skin color condition is in the best condition and the worst condition, related to the eye area that is the fixed-point observation point.

In Step S103, the measurement result analysis unit 86 controls the information control unit 85 and reads and acquires, from the memory 57, face images obtained when the skin condition satisfying the comparing conditions is measured. The measurement result analysis unit 86 outputs the acquired face images to the display control unit 87.

In Step S104, the display control unit 87 displays the face images supplied from the measurement result analysis unit 86 side by side on the display 11.

FIG. 29 is a diagram illustrating an exemplary face image display screen.

A face image 201 and a face image 202 are displayed side by side on the display screen in FIG. 29. The left-side face image 201 is a face image photographed in measurement on Jan. 1, 2014. The right-side face image 202 is a face image photographed in measurement on Jan. 8, 2014.

For example, the face image 201 is the image obtained when the best condition is measured as the skin color condition in the eye area that is the fixed-point observation point. On the other hand, the face image 202 is the image obtained when the worst condition is measured as the skin color condition in the eye area that is the fixed-point observation point.

Based the above display, a user can compare the face image obtained when dark circles around the eyes (skin color) are in the best condition with the face image obtained when the dark circles around the eyes are in the worst condition. The comparing conditions are not limited those described above. The user can also select other comparing conditions such as texture levels, and comparison can be made between face images obtained when the skin condition satisfying the comparing conditions are measured.

The user can confirm, for example, temporal change of the face, change of facial expression, change of makeup, change of skin before and after treatment such as massage by using the face image comparing function. The temporal change of the face includes change of a face line, change of sagging, change of wrinkles, and change of blemishes (darkness level/size). The facial expression includes angle change of a mouth corner, positional change of the mouth corner, and change of the way of smile. The change of makeup includes change of an eyebrow shape, positional change of cheek powder application, color change of eye shadow, a lipstick, foundation, and the like.

Face Image Searching Function

A face image searching function is a function to make a search for a face image obtained when skin condition satisfying a condition designated by a user is measured.

Figure 30:
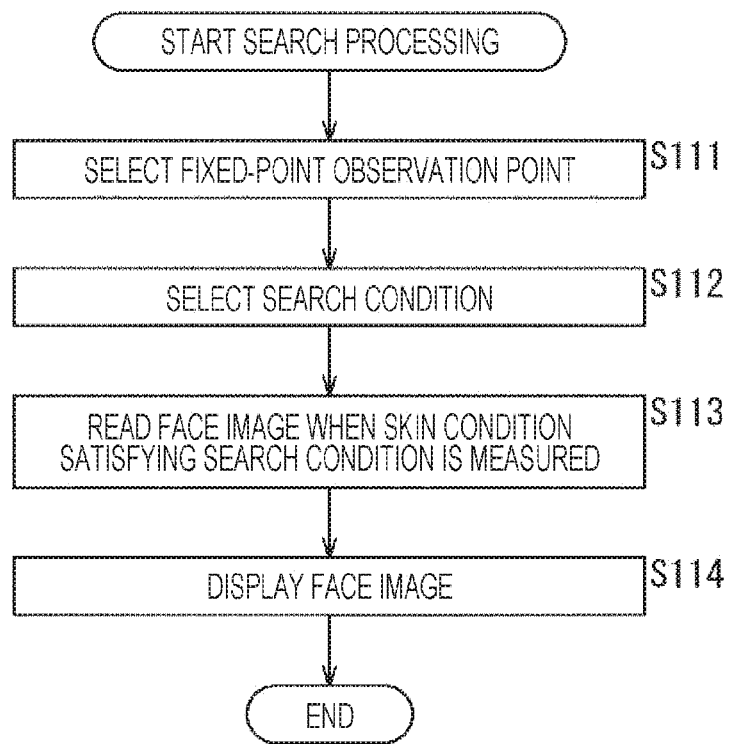
FIG. 30 is a flowchart to describe search processing.

The face image search processing will be described with reference to a flowchart of FIG. 30.

In Step S111, the measurement result analysis unit 86 selects a fixed-point observation point. The measurement result analysis unit 86 selects a predetermined fixed-point observation point from among a plurality of fixed-point observation points in accordance with, for example, user's operation on a selection screen.

In Step S112, the measurement result analysis unit 86 selects a search condition related to skin condition at the fixed-point observation point selected in Step S101. For example, in accordance with the user's operation, the measurement result analysis unit 86 selects a condition, such as that a skin color is pink, related to the cheek that is the fixed-point observation point. In the case of measuring skin condition after makeup is applied, various kinds of colors may be measured as a skin color.

In Step S113, the measurement result analysis unit 86 controls the information control unit 85, and reads and acquires, from the memory 57, a face image obtained when skin condition satisfying the search condition is measured. The measurement result analysis unit 86 outputs the acquired face images to the display control unit 87.

In Step S114, the display control unit 87 displays, on the display 11, the face image supplied from the measurement result analysis unit 86.

Figure 31:
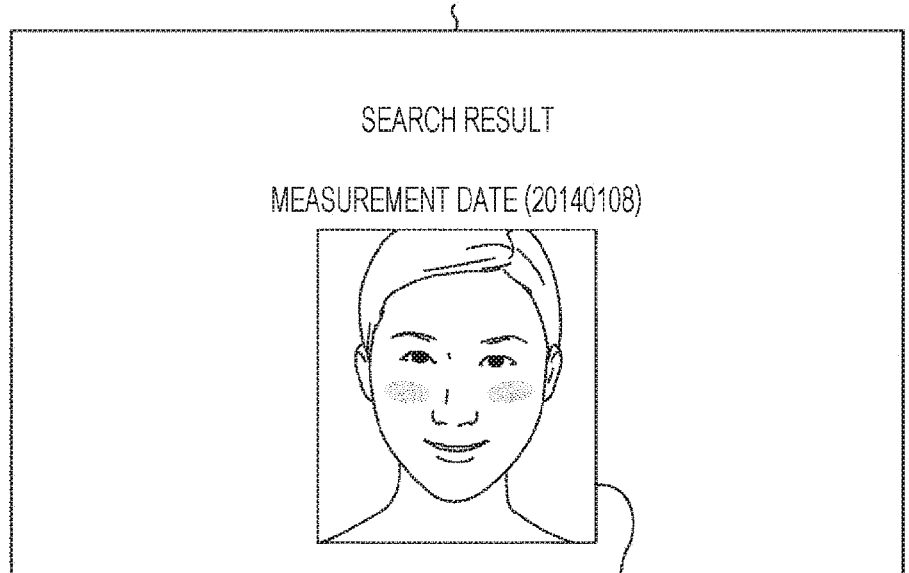
FIG. 31 is a diagram illustrating an exemplary face image display screen.

FIG. 31 is a diagram illustrating an exemplary face image display screen.

A face image 211 is displayed on the display screen in FIG. 31. The face image 211 is a face image photographed at the time of measurement on Jan. 8, 2014.

For example, the face image 211 is a face image obtained when the cheek skin color that is the fixed-point observation point is measured as pink.

Based on this display, the user can confirm the face image obtained when pink makeup is applied on the cheeks. The search condition is not limited to the above-described one. The user can confirm face images of various kinds of skin condition by using the skin condition as a search key.

Improvement Method Presenting Function

An improvement method presenting function is a function to present an excising method to improve skin condition to a user. In the case where the user performs the presented excise, whether the excise performed by the user is correct is evaluated by the information processing device 1.

The improvement method presenting processing will be described with reference to a flowchart of FIG. 32.

In order to evaluate the excise performed by the user, the information processing device 1 is needed to recognize which portion of the face and how the user moves. Before evaluating the excise, the information processing device 1 adjusts a relation between a face of the user and the information processing device 1 same as the relation at the time of initial setting in the similar manner at the time of measuring the skin condition.

Figure 32:
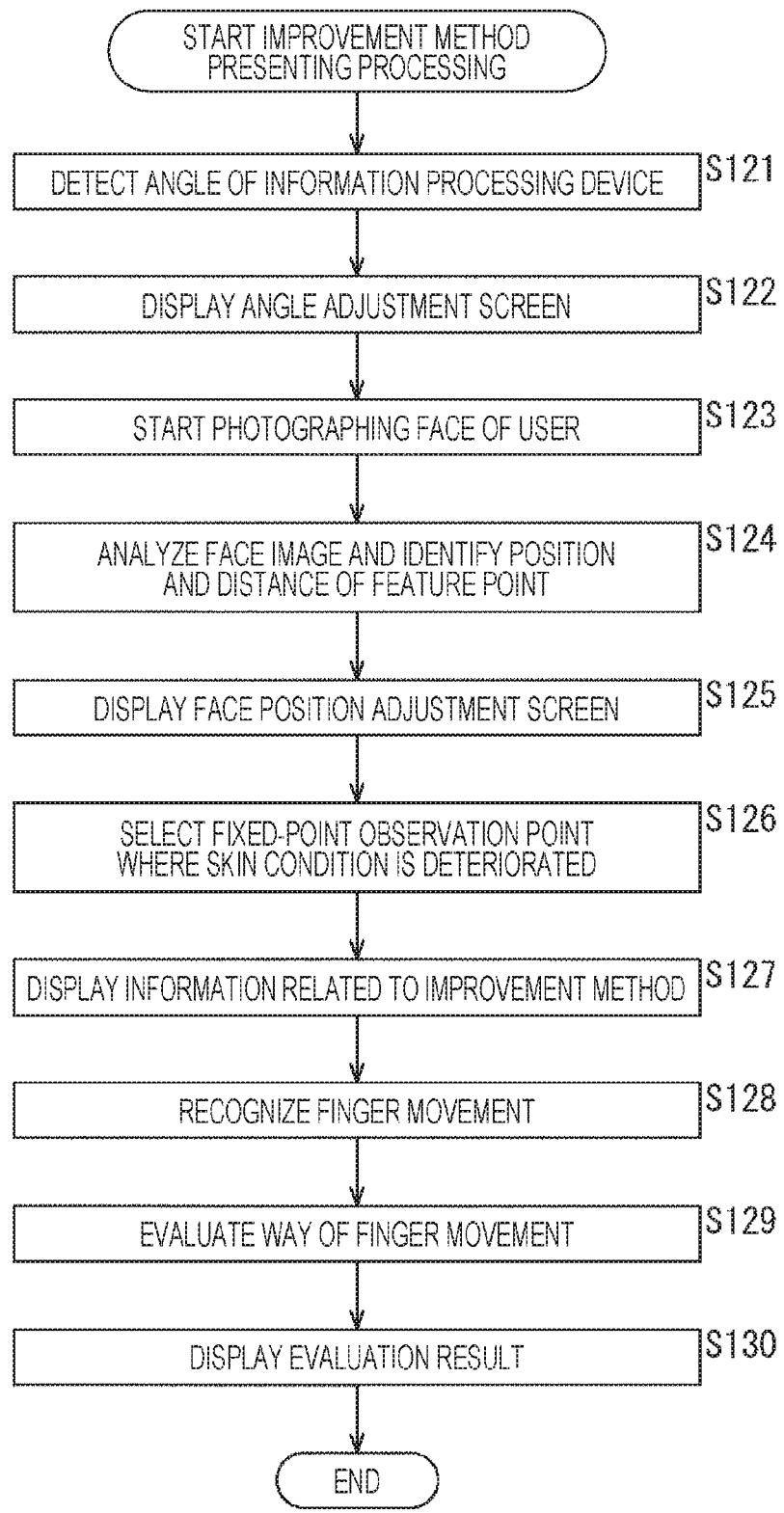
FIG. 32 is a flowchart to describe improvement method presenting processing.

The processing in Steps S121 to S125 of FIG. 32 is the processing similar to the processing in Steps S41 to 45 of FIG. 15. Repetition of the same description will be suitably omitted.

In Step S121, the angle sensor 59 detects an angle of the information processing device 1.

In Step S122, in the case where an angle detected by the angle sensor 59 differs from an angle at the time of initial setting, the display control unit 87 displays an angle adjustment screen on the display 11.

In Step S123, the image acquisition unit 81 controls the camera 12 and starts photographing a face of a user.

In Step S124, the recognition unit 82 analyzes the face image, and identifies a position of a feature point on the face image as well as a distance to each feature point. Identifying a position of a feature point and a distance to each feature point is repeatedly performed.

In Step S125, the display control unit 87 displays a face position adjustment screen on the display 11.

In Step S126, the measurement result analysis unit 86 selects, on the basis of measurement results during a predetermined period, a fixed-point observation point where the skin condition is deteriorated.

In Step S127, the display control unit 87 displays, on the display 11, information related to a skin improvement method at the fixed-point observation point where the skin condition is deteriorated. For example, in the case where a skin temperature at the cheek that is the fixed-point observation point is deteriorated, the display control unit 87 displays how to perform excise in order to improve the skin temperature at the cheek.

Information related to exercises to improve the skin condition at respective portions of the face is recorded in the memory 57. The display control unit 87 selects and displays: the fixed-point observation point where the skin condition is deteriorated; and information corresponding to a deteriorated item. The user confirms the information displayed on the display 11, and performs a presented excise. Most of excises are to provide massage on the face with fingertips.

In Step S128, the recognition unit 82 analyzes the face image supplied from the image acquisition unit 81, and recognizes finger movement of the user. The finger movement of the user is recognized by change of positions of the fingertips on the face image. The positions of the fingertips in each timing are also represented while setting the positions of the feature points as references. Information indicating finger movement recognized by the recognition unit 82 is supplied to the display control unit 87.

In Step S129, the display control unit 87 identifies a way of finger movement of the user on the basis of the information supplied from the recognition unit 82, and evaluates whether the way of movement is correct. In the case where the way of excise is not correct, the skin condition may be deteriorated. For example, information indicating a correct way of movement and information indicating an incorrect way of movement are recorded in the memory 57 for each excise. The display control unit 87 evaluates the excise performed by the user on the basis of the information recorded in the memory 57.

In Step S130, the display control unit 87 displays an evaluation result on the way of finger movement of the user on the display 11.

Figure 33:
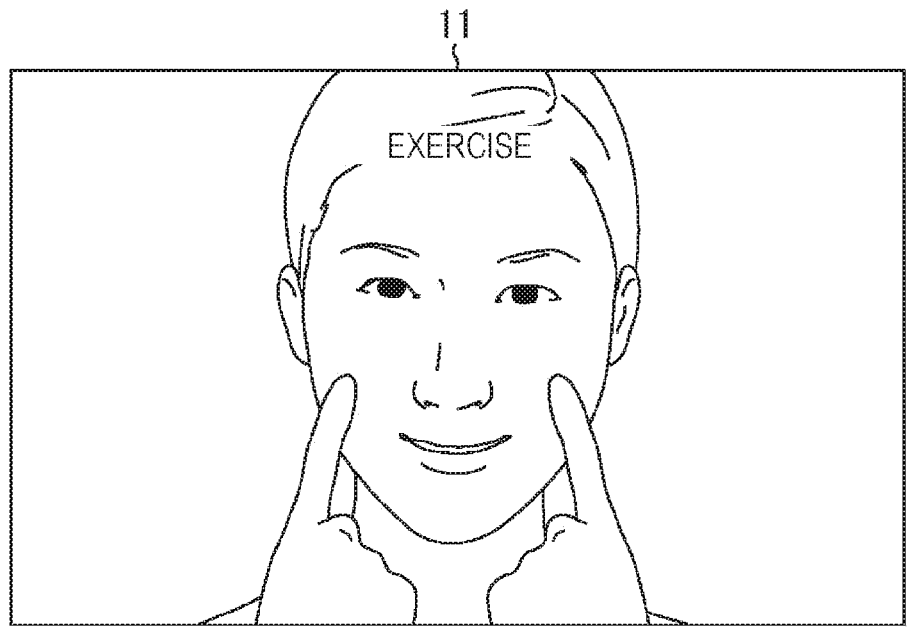
FIG. 33 is a diagram illustrating an exemplary face image.

FIG. 33 is a diagram illustrating an exemplary face image of a user who is performing exercise.

In the example of FIG. 33, a user is massaging areas near the cheeks with forefingers of both hands. Such a way of finger movement is recognized, and whether the way of finger movement is correct is evaluated.

Figure 34:
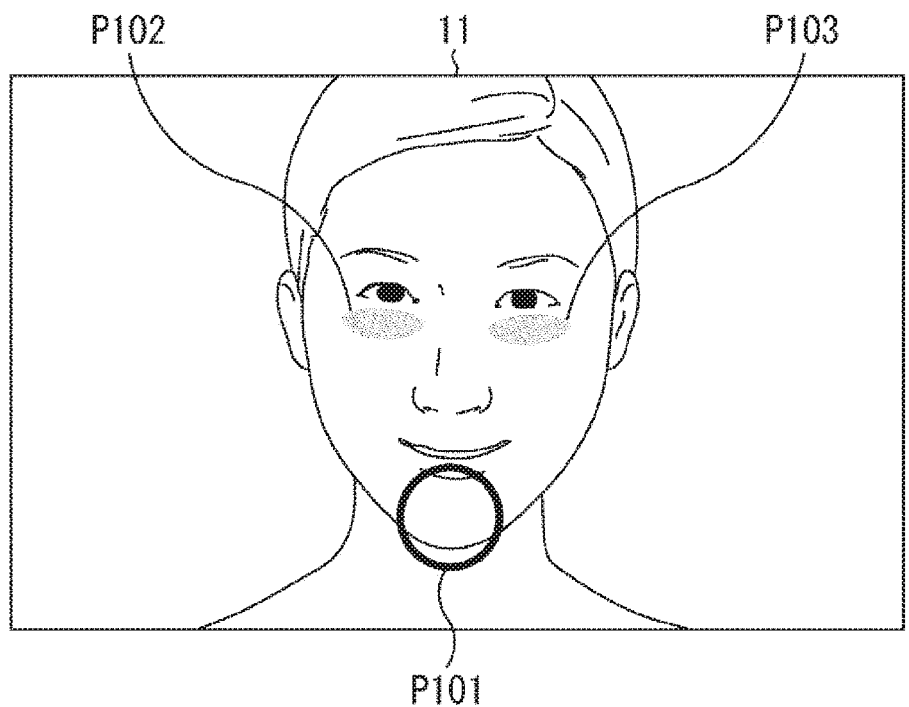
FIG. 34 is a diagram illustrating examples of evaluation result display.

FIG. 34 is a diagram illustrating examples of evaluation result display.

In the case where the way of finger movement is evaluated as correct, an image P101 indicating that the way of finger movement is correct is displayed in a manner superimposed on the face image as illustrated in FIG. 34. Images P102 and P103 displayed in a manner superimposed on the eye areas indicate portions where a skin temperature is to be improved by exercise performed by the user.

Figure 35:
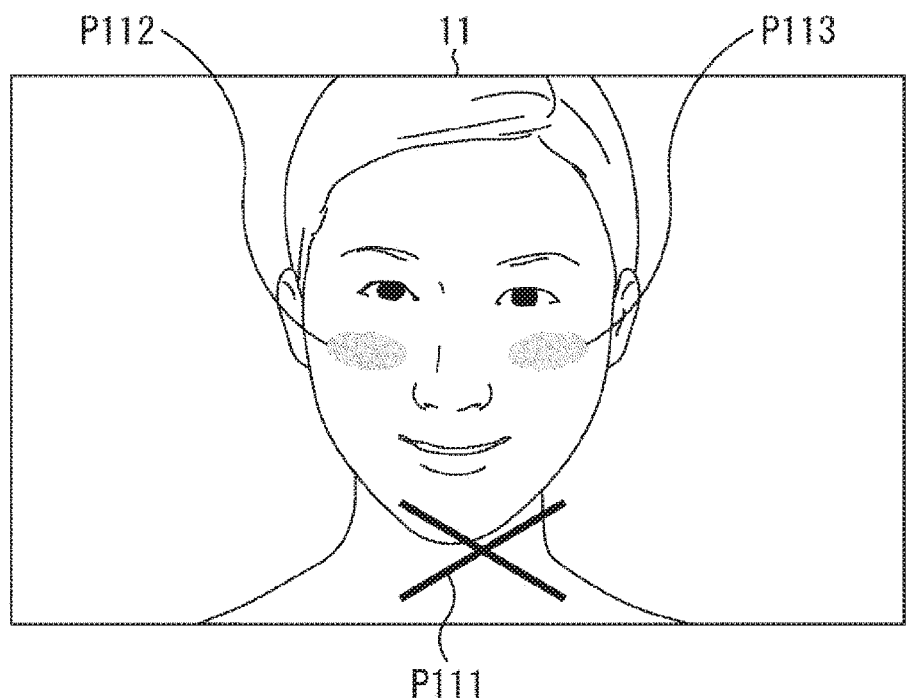
FIG. 35 is a diagram illustrating other examples of the evaluation result display.

FIG. 35 is a diagram illustrating other examples of the evaluation result display.

In the case where the way of finger movement is evaluated as incorrect, an image P111 indicating that the way of finger movement is incorrect is displayed in a manner superimposed on the face image as illustrated in FIG. 35. Images P112 and P113 displayed in a manner superimposed on positions of the cheeks close to the eye areas indicate portions where a skin temperature is lowered by exercise performed by the user.

With the above-described processing, the user can correctly perform exercise at a fixed-point observation point where the skin condition is deteriorated.

Searching Function for Portion Having Deteriorated Skin Condition

Search processing will be described with reference to a flowchart of FIG. 36.

Figure 36:
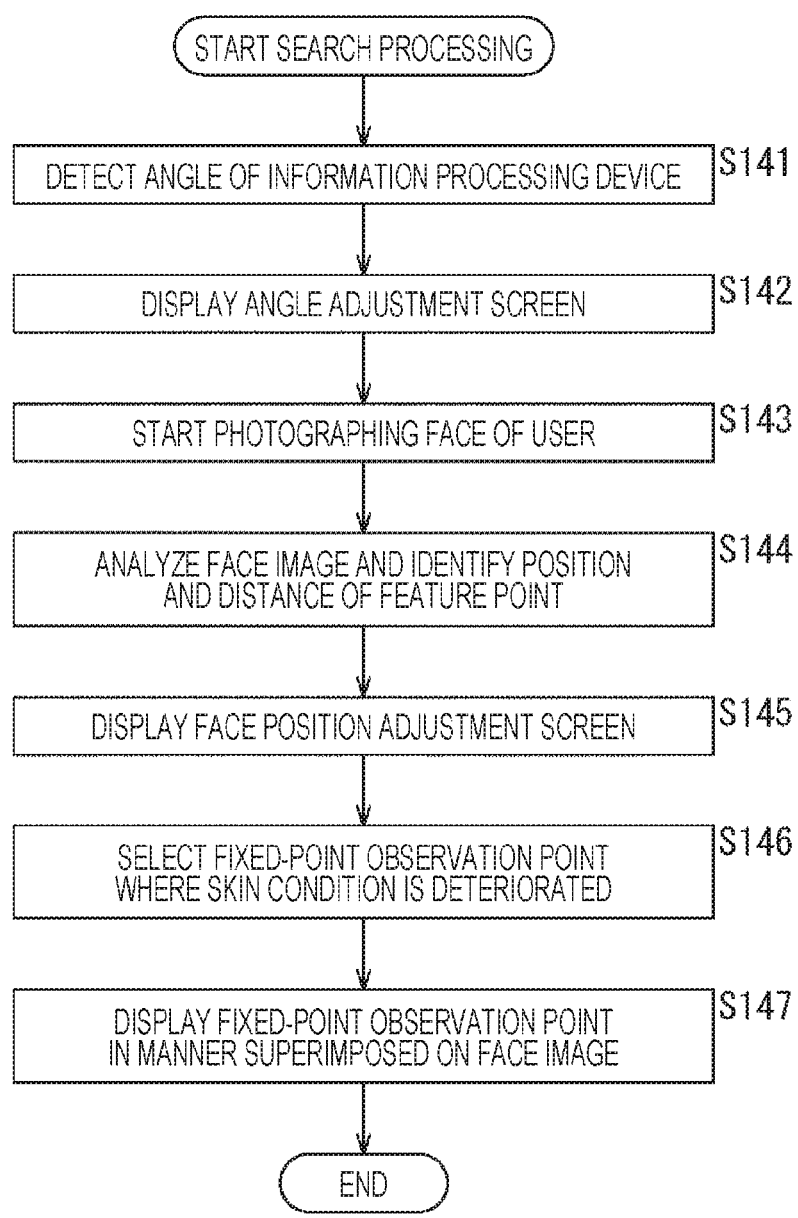
FIG. 36 is a flowchart to describe search processing.

Processing in Steps S141 to S146 in FIG. 36 is similar processing to the processing in Steps S121 to 126 in FIG. 32. Repetition of the same description will be suitably omitted.

In Step S141, the angle sensor 59 detects an angle of the information processing device 1.

In Step S142, in the case where an angle detected by the angle sensor 59 differs from an angle at the time of initial setting, the display control unit 87 displays an angle adjustment screen on the display 11.

In Step S143, the image acquisition unit 81 controls the camera 12 and starts photographing a face of a user.

In Step S144, the recognition unit 82 analyzes the face image, and identifies a position of a feature point on the face image as well as a distance to each feature point. Identifying a position of a feature point and a distance to each feature point is repeatedly performed.

In Step S145, the display control unit 87 display a face position adjustment screen on the display 11.

In Step S146, the measurement result analysis unit 86 selects, on the basis of measurement results during a predetermined period, a fixed-point observation point where the skin condition is deteriorated.

In Step S147, the display control unit 87 displays the fixed-point observation point where the skin condition is deteriorated in a manner superimposed on a face image.

Figure 37:
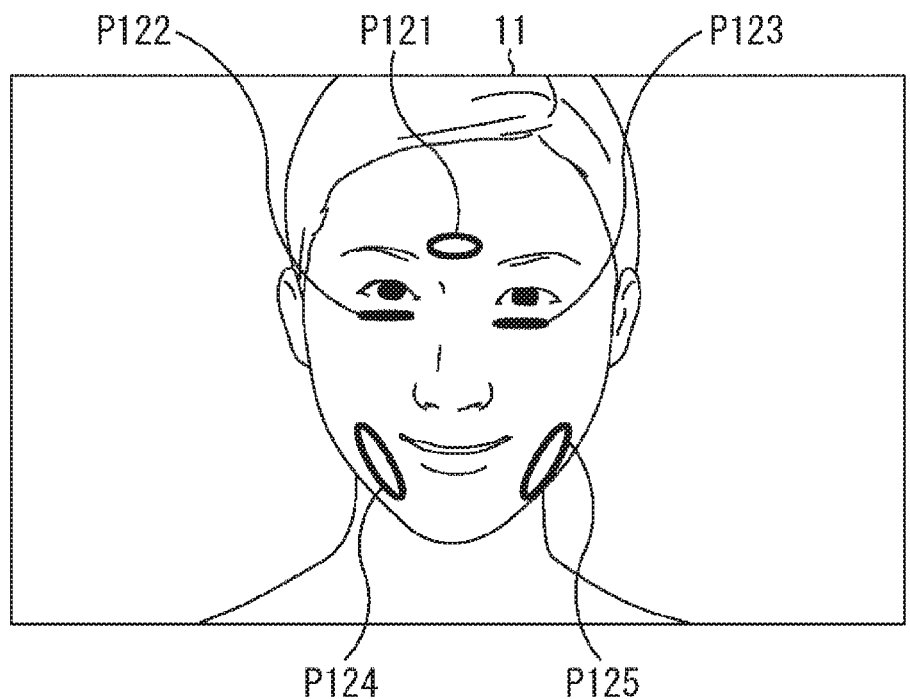
FIG. 37 is a diagram illustrating an exemplary display of a face image.

FIG. 37 is a diagram illustrating an exemplary display of a face image.

The face image in FIG. 37 is a moving image photographed by the camera 12. Information indicating deterioration of skin condition at a fixed-point observation point, such as decrease of a blood flow rate and decrease of a skin temperature, is displayed in a manner superimposed on the face image. Each of images P121 to P125 indicates a fixed-point observation point where the skin condition is deteriorated during the predetermined period. The images P121 to P125 are displayed in a manner changing positions thereof in accordance with face movement of the user.

With the above-described processing, the user can collectively confirm places where the skin condition is deteriorated. A search for a fixed-point observation point where skin condition is improved may also be made instead of making a search for a fixed-point observation point where skin condition is deteriorated, and a search result thereof may be presented to the user.

Person Searching Function

A person searching function is a function to make a search for a person having a feature point position on a face similar to that of a user. In the case where an information processing device 1 is provided in a beauty salon and the like, a plurality of users uses the information processing device 1 and performs fixed-point observation on skin condition. Setting information that includes positional information of feature points on faces of a plurality of persons is accumulated in the information processing device 1. A person search is made by using the setting information accumulated in the information processing device 1.

Figure 38:
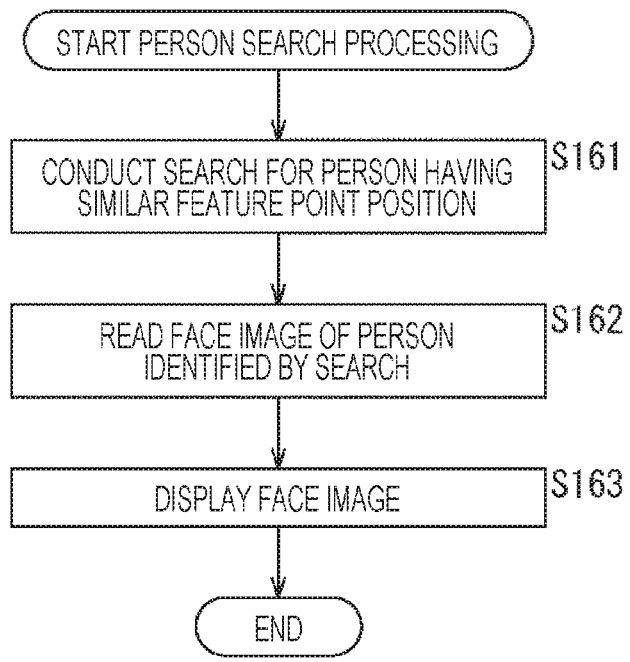
FIG. 38 is a flowchart to describe person search processing.

The person search processing will be described with reference to a flowchart of FIG. 38.

In Step S161, the display control unit 87 refers to the information recorded in the memory 57 and makes a search for a person who has a feature point position on the face similar to that of a user who is currently using the information processing device 1.

In Step S162, the display control unit 87 reads, from the memory 57, a face image of a person identified by the search.

In Step S163, the display control unit 87 displays a face image of the user who is currently using the information processing device 1 and the face image read from the memory 57.

Figure 39:
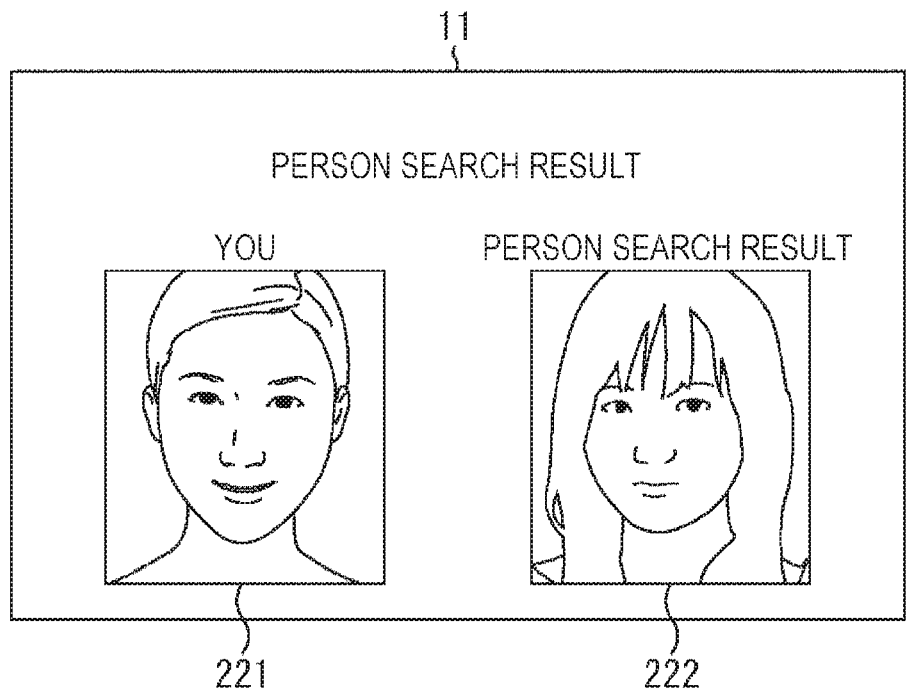
FIG. 39 is a diagram illustrating an exemplary face image display screen.

FIG. 39 is a diagram illustrating an exemplary face image display screen.

A face image 221 and a face image 222 are displayed side by side on the display screen in FIG. 39. The left-side face image 221 is a face image of the user currently using the information processing device 1. The right-side face image 222 is a face image of a person retrieved from the search as a person having a feature point position similar to that of the user currently using the information processing device 1.

The user can refer to the skin condition, the way of makeup, and the like of the person having the feature similar to that of own face.

Hair Style Simulating Function

A hair style simulating function is a function to display a hair portion on a face image photographed by the camera 12 in a manner synthesized with various kinds of hair style images prepared in advance.

Figure 40:
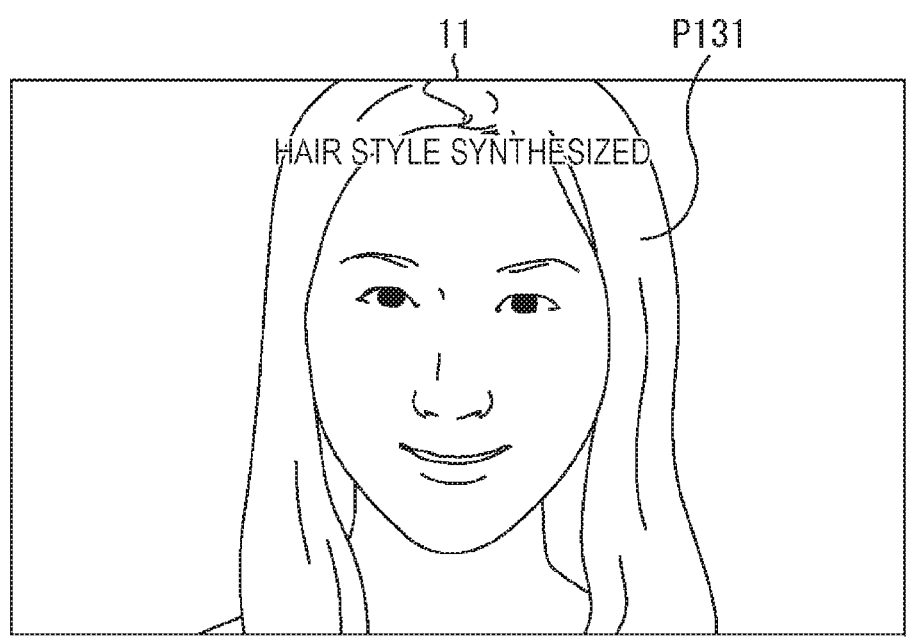
FIG. 40 is a diagram illustrating an exemplar display as a result of synthesizing a hair style.

FIG. 40 is a diagram illustrating an exemplar display as a result of synthesizing a hair style.

The face image in FIG. 40 is a moving image photographed by the camera 12. For example, a hair position shown in each frame of the moving image is identified on the basis of a position of a feature point on a face of a user, and an image P131 is synthesized at the identified position. The image P131 is a hair style image selected by the user from among a plurality of those prepared in advance. The user can switch a hair style image to be synthesized as the image P131.

5. Modified Example

While it has been described that a camera adapted to photograph a face image is provided in the information processing device 1, a face image may also be photographed by a camera separated from the information processing device 1.

Furthermore, while it has been described that a display adapted to display various kinds of information is provided in the information processing device 1, various kinds of screens may also be displayed on a display separated from the information processing device 1.

While it has been described that skin condition of a face is measured by using a skin measurement system in FIG. 1, a portion to be subjected to skin condition measurement may also be portions other than the face, such as a hand, an arm, and a foot. For example, in the case of performing fixed-point observation on skin condition of the hand, a nail, a fingertip, and the like are recognized as feature points.

While it has been described that a series of processing including recognition of a feature point on a face, analysis on skin condition, and analysis on a fixed-point observation result is performed by the information processing device 1, the processing may also be performed by a server connected to a network such as the internet.

In this case, the information processing device 1 and the server are connected via the network. The configuration described with reference to FIG. 6 is implemented in the server.

The information processing device 1 transmits a face image and a skin image to the server at the time of measuring skin condition. The server receives and acquires the face image and the skin image transmitted from the information processing device 1. The server generates data for the above-described various kinds of screens by analyzing the face image, and transmits the data to the information processing device 1. The information processing device 1 displays, on the display 11, the various kinds of screens on the basis of the data transmitted from the server.

Furthermore, the server analyzes the skin image, and measures and records skin condition. In the case where a result of fixed-point observation is requested, the server analyzes change of the skin condition on the basis of measurement results of respective measurement, and transmits the result of fixed-point observation to the information processing device 1. The information processing device 1 displays, on the display 11, the result of fixed-point observation on the basis of the data transmitted from the server.

Exemplary Configuration of Computer

The above-described series of processing can be executed by hardware and also can be executed by software. In the case of executing the series of processing by the software, a program constituting the software is installed from a program recording medium in, for example, a computer incorporated in dedicated hardware or a general-purpose personal computer.

The program to be installed is provided by being recorded in a removable medium 61 illustrated in FIG. 5 formed of an optical disc (compact disc-read only memory (CD-ROM), digital versatile disc (DVD), and the like) a semiconductor memory and the like. Furthermore, the program may also be provided via a wired or wireless transmission medium, such as a local area network, the internet, and digital broadcasting. The program can be preliminarily installed in a ROM 52 or a memory 57.

Meanwhile, the program executed by a computer may be a program in which processing is performed in time series in the order described in the present specification or may be a program in which processing is performed in parallel or at necessary timing such as when the program is called.

Note that, in the present specification, the system means an assembly including a plurality of constituent elements (devices, modules (parts), and the like), and whether all of the constituent elements are located in a same housing is disregarded. Therefore, any one of a plurality of devices connected via a network and housed in different housings and a device having a plurality of modules housed in a single housing corresponds to the system.

Note that the above effects described in the present specification are only examples and not limited thereto, and other effects may also be provided.

An embodiment of the present technology is not limited to the above-described embodiment, and various kinds of modifications can be made within a range not departing from a gist of the present technology.

For example, the present technology can have a cloud computing configuration in which processing is performed sharing one function with a plurality of devices via a network in a collaborative manner.

Furthermore, each of the steps described in the above-described flowcharts can be executed not only by one device but also by a plurality of devices in a sharing manner.

Moreover, in the case where a plurality of processing is included in one step, the plurality of processing included in this one step can be executed not only by one device but also by the plurality of devices in a sharing manner.

Exemplary Combination of Configurations

The present technology can also have following configurations.

(1)

An information processing device including:

an acquisition unit adapted to acquire an image that shows a predetermined feature point of a user who is a measurer of skin condition, and a measurement portion of skin condition;

a recognition unit adapted to analyze the image and recognize a position of the feature point; and a display control unit adapted to display information indicating the measurement portion at a predetermined position on the image while setting, as a reference, the position of the feature point recognized by the recognition unit.

(2)

The information processing device recited in above (1), further including a photographing unit adapted to photograph the image, wherein the acquisition unit acquires the image photographed by the photographing unit.

(3)

The information processing device recited in above (1) or (2), further including a display unit adapted to display the image and the information indicating the measurement portion.

(4)

The information processing device recited in any one of above (1) to (3), further including a setting unit adapted to set the measurement portion at the predetermined position while setting, as a reference, the position of the feature point recognized by the recognition unit by analyzing the image photographed at the time of setting the measurement portion.

(5)

The information processing device recited in any one of above (1) to (3), further including a setting unit adapted to set the measurement portion at a position designated by the user on the image photographed at the time of setting the measurement portion.

(6)

The information processing device recited in above (4) or (5), further including a detection unit adapted to detect an angle of the information processing device at the time of setting the measurement portion.

(7)

The information processing device recited in above (6), wherein the display control unit displays information that provides a guide on adjusting an angle of the information processing device to an angle same as the angle detected by the detection unit.

(8)

The information processing device recited in any one of above (1) to (7), wherein the display control unit displays, on the image, information indicating the feature point at a position same as the position of the feature point recognized by the recognition unit by analyzing the image photographed at the time of setting the measurement portion.

(9)

The information processing device recited in any one of above (1) to (8), wherein the display control unit changes a display position of the information indicating the measurement portion in accordance with change of the position of the feature point.

(10)

The information processing device recited in any one of above (1) to (9), wherein the acquisition unit acquires a skin image obtained by photographing skin of the measurement portion, and the display control unit displays the skin image and the image showing the user at the same time.

(11)

The information processing device recited in above (10), further including:

an analysis unit adapted to analyze the skin image and measure skin condition of the measurement portion; and a recording unit adapted to record information indicating a measurement result obtained by the analysis unit.

(12)

The information processing device recited in above (11), wherein the display control unit displays information indicating change of skin condition of the measurement portion on the basis of information indicating results obtained plural times of measurement recorded in the recording unit.

(13)

An information processing method including steps of:

acquiring an image that shows a predetermined feature point of a user who is a measurer of skin condition, and a measurement portion of skin condition;

analyzing the image and recognizing a position of the feature point; and displaying information indicating the measurement portion at a predetermined position on the image while setting, as a reference, the recognized position of the feature point.

(14)

A program causing a computer to execute processing including steps of:

acquiring an image that shows a predetermined feature point of a user who is a measurer of skin condition, and a measurement portion of skin condition;

analyzing the image and recognizing a position of the feature point; and displaying information indicating the measurement portion at a predetermined position on the image while setting, as a reference, the recognized position of the feature point.

REFERENCE SIGNS LIST

1 Information processing device
2 Skin measurement device
11 Display
12 Camera
81 Image acquisition unit
82 Recognition unit
83 Skin condition analysis unit
84 Fixed-point observation point setting unit
85 Information control unit
86 Measurement result analysis unit
87 Display control unit

The invention claimed is:

1. An information processing device, comprising:
a display unit; and
circuitry configured to:
  determine a relation between a user face position and a position of the information processing device;
  display a first guide screen on the display unit to adjust the relation between the user face position and the position of the information processing device;
  acquire a user face image based on the adjusted relation, wherein the user face image includes a user feature point and a measurement portion of user skin;
  analyze the user face image;
  determine each of a position of the user feature point on the user face image and a distance of the user feature point from the information processing device based on the analysis of the user face image;
  display a second guide screen on the display unit to adjust the position of the user feature point on the user face image to an updated position of the user feature point and the distance of the user feature point from the information processing device to an updated distance of the user feature point from the information processing device,
  wherein the second guide screen is displayed based on a position of a specific user feature point on the user face image and a distance of the specific user feature point from the information processing device; and
  display information on the display unit, wherein
    the information indicates the measurement portion at a specific position on the user face image, and
    the specific position on the user face image corresponds to the updated position of the user feature point on the user face image and the updated distance of the user feature point from the information processing device.

2. The information processing device according to claim 1, wherein the circuitry is further configured to photograph the user face image.

3. The information processing device according to claim 1, wherein the display unit is further configured to display the user face image.

4. The information processing device according to claim 1, wherein the circuitry is further configured to set the measurement portion at the position of the user feature point based on the analyzed user face image.

5. The information processing device according to claim 4, wherein the circuitry is further configured to detect an angle of the information processing device.

6. The information processing device according to claim 5, wherein
the circuitry is further configured to display a third guide screen on the display unit, and
the third guide screen includes information to adjust the angle of the information processing device to a specific angle.

7. The information processing device according to claim 1, wherein the circuitry is further configured to set the measurement portion at a user designated position on the user face image.

8. The information processing device according to claim 1, wherein the information is superimposed on the user face image.

9. The information processing device according to claim 1, wherein the circuitry is further configured to change a display position of the displayed information based on a change of the position of the user feature point on the user face image.

10. The information processing device according to claim 1, wherein the circuitry is further configured to:
photograph skin of the measurement portion to acquire a user skin image; and
concurrently display the user skin image and the user face image.

11. The information processing device according to claim 10, wherein the circuitry is further configured to:
analyze the user skin image;
measure a skin condition of the measurement portion; and
store a specific measurement result of a plurality of measurement results, wherein the specific measurement result is based on the analyzed user skin image and measured skin condition.

12. The information processing device according to claim 11, wherein
the circuitry is further configured to display specific information, and
the specific information indicates a change of the skin condition based on the plurality of measurement results.

13. An information processing method, comprising:
in an information processing device:
determining a relation between a user face position and a position of the information processing device;
displaying a guide screen on a display unit of the information processing device to adjust the relation between the user face position and the position of the information processing device;
acquiring a user face image based on the adjusted relation, wherein the user face image includes a user feature point and a measurement portion of user skin;
analyzing the user face image;
determining each of a position of the user feature point on the user face image and a distance of the user feature point from the information processing device based on the analysis of the user face image;
displaying a second guide screen on the display unit to adjust the position of the user feature point on the user face image and the distance of the user feature point from the information processing device,
wherein the second guide screen is displayed based on a position of a specific user feature point on the user face image and a distance of the specific user feature point from the information processing device; and
displaying information on the display unit, wherein
the information indicates the measurement portion at a specific position on the user face image, and
the specific position on the user face image corresponds to the adjusted position of the user feature point on the user face image and the adjusted distance of the user feature point from the information processing device.

14. A non-transitory computer-readable medium having stored thereon computer-executable instructions which, when executed by a computer, cause the computer to execute operations, the operations comprising:
determining a relation between a user face position and a position of an information processing device;
displaying a guide screen on a display unit of the information processing device to adjust the relation between the user face position and the position of the information processing device;
acquiring a user face image based on the adjusted relation, wherein the user face image includes a user feature point and a measurement portion of user skin;
analyzing the user face image;
determining each of a position of the user feature point on the user face image and a distance of the user feature point from the information processing device based on the analysis of the user face image;
displaying a second guide screen on the display unit to adjust the position of the user feature point on the user face image and the distance of the user feature point from the information processing device,
wherein the second guide screen is displayed based on a position of a specific user feature point on the user face image and a distance of the specific user feature point from the information processing device; and
displaying information on the display unit, wherein
the information indicates the measurement portion at a specific position on the user face image, and
the specific position on the user face image corresponds to the adjusted position of the user feature point on the user face image and the adjusted distance of the user feature point from the information processing device.

* * * * *